United States Patent [19]

Nelson et al.

[11] Patent Number: 5,663,187

[45] Date of Patent: Sep. 2, 1997

[54] TREATMENT OF ATHEROSCLEROSIS WITH ANGIOTENSIN II RECEPTOR BLOCKING IMIDAZOLES

[75] Inventors: Edward B. Nelson, Lower Gwynedd; Charles S. Sweet, Ambler, both of Pa.

[73] Assignee: Merck & Co., Inc., Rahway, N.J.

[21] Appl. No.: 466,484

[22] Filed: Jun. 6, 1995

Related U.S. Application Data

[62] Division of Ser. No. 219,685, Mar. 29, 1994, abandoned.

[51] Int. Cl.$^6$ .......... A61K 31/41; A61K 31/35; A61K 31/235
[52] U.S. Cl. .......... 514/381; 514/460; 514/547
[58] Field of Search .......... 514/381, 460, 514/547

[56] References Cited

U.S. PATENT DOCUMENTS

| | | | |
|---|---|---|---|
| 4,444,784 | 4/1984 | Hoffman et al. | 424/279 |
| 5,138,069 | 8/1992 | Carini et al. | 548/253 |
| 5,162,340 | 11/1992 | Chakravarty et al. | 514/309 |
| 5,214,153 | 5/1993 | Chen et al. | 548/252 |
| 5,218,125 | 6/1993 | Chen et al. | 548/252 |
| 5,225,428 | 7/1993 | Kramer et al. | 514/381 |

FOREIGN PATENT DOCUMENTS

| | | |
|---|---|---|
| 0 457 514 A1 | 11/1991 | European Pat. Off. . |
| 0 475 206 A2 | 3/1992 | European Pat. Off. . |
| 0 513 533 A2 | 11/1992 | European Pat. Off. . |
| 0 535 463 A1 | 4/1993 | European Pat. Off. . |
| 0 535 465 A1 | 4/1993 | European Pat. Off. . |
| 0 539 713 A1 | 5/1993 | European Pat. Off. . |
| WO 92/04343 | 3/1992 | WIPO . |
| WO 92/20342 | 11/1992 | WIPO . |
| WO 93/04045 | 3/1993 | WIPO . |
| WO 93/04046 | 3/1993 | WIPO . |
| WO 93/15734 | 8/1993 | WIPO . |
| WO 94/04153 | 3/1994 | WIPO . |

OTHER PUBLICATIONS

Mol et al., "Effects of Synvinolin (MK–733) on Plasma Lipids in Familial Hypercholesterolemia,"The Lancet, Oct. 25, 1986, vol. II, pp. 936–939.

The Merck Manual, 1987, pp. 386–389.

*Primary Examiner*—Richard L. Raymond
*Assistant Examiner*—Mary C. Cebulak
*Attorney, Agent, or Firm*—Valerie J. Camara; Mark R. Daniel

[57] ABSTRACT

A method of treatment for atherosclerosis and/or reducing cholesterol using an angiotensin II antagonist. This method of treatment can be used in conjunction with the treatment of hypertension. Substituted imidazoles such as

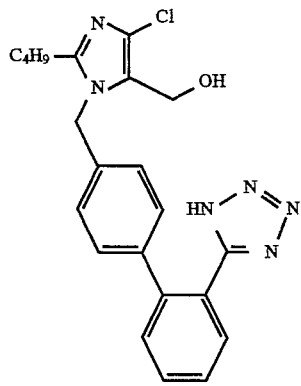

are useful as angiotensin II receptor antagonists for this method of treatment. A method of treatment for atherosclerosis and/or reducing cholesterol using an angiotensin II receptor antagonist in combination with an HMG-Co A reductase inhibitor. A method of treatment for atherosclerosis and/or reducing cholesterol using an angiotensin II receptor antagonist in combination with an HMG-Co A reductase inhibitor and an angiotensin converting enzyme inhibitor. Also within the scope of this invention are pharmaceutical compositions for this method of use.

2 Claims, No Drawings

TREATMENT OF ATHEROSCLEROSIS WITH ANGIOTENSIN II RECEPTOR BLOCKING IMIDAZOLES

This is a division of application Ser. No. 08/219,685 filed Mar. 29, 1994, now abandoned.

BACKGROUND OF THE INVENTION

This invention relates to a novel method of using an angiotensin II antagonist, such as substituted imidazole compounds, for the treatment of atherosclerosis and/or reducing cholesterol, alone or in conjunction with the treatment of hypertension. The invention also relates to using an angiotensin II antagonist in combination with a 3-hydroxy-3-methylglutaryl coenzyme A reductase inhibitor (HMG-Co A reductase inhibitor). The invention also relates to using an angiotensin II antagonist in combination with an HMG-Co A reductase inhibitor and an angiotensin converting enzyme inhibitor. The invention also relates to compositions useful for this method of treatment.

The compounds of this invention are known to inhibit the action of the octapeptide hormone angiotensin II (II) and are useful therefore in alleviating angiotensin induced hypertension. The enzyme renin acts on a blood plasma $\alpha_2$-globulin, angiotensinogen, to produce angiotensin I, which is then converted by angiotensin converting-enzyme to AII. The latter substance is a powerful vasopressor agent which has been implicated as a causitive agent for producing high blood pressure in various mammalian species, such as the rat, dog, and man. The angiotensin II antagonist compounds inhibit the action of AII at its receptors on target cells and thus prevent the increase in blood pressure produced by this hormone-receptor interaction. By administering an angiotensin II antagonist compound, such as a compound of formula I, to a species of mammal with atherosclerosis and/or high cholesterol and/or hypertension due to AII, the blood pressure is reduced. The compounds of formula I are also useful for the treatment of high cholesterol by reducing the total cholesterol. Administration of a compound of formula I with a diuretic such as furosemide or hydrochlorothiazide, either as a stepwise combined therapy (diuretic first) or as a physical mixture, enhances the antihypertensives effect of the compound, while also treating atherosclerosis and reducing cholesterol levels. Administration of an angiotensin II receptor antagonist, such as a compound of formula I, with an HMG-Co A reductase inhibitor, such as the compounds of formula II, either as a stepwise combined therapy or as a physical mixture, may enhance the treatment of atherosclerosis and/or the reduction cholesterol levels, while also treating hypertension.

K. Matsumura, et. al., in U.S. Pat. No. 4,207,324 issued Jun. 10, 1980, discloses 1,2-disubstituted-4-haloimidazole-5-acetic acid derivatives of the formula:

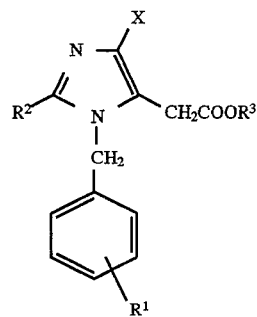

Wherein $R^1$ is hydrogen, nitro or amino; $R^2$ is phenyl, furyl or thienyl optionally substituted by halogen, lower alkyl, lower alkoxy or di-lower alkylamino; $R^3$ is hydrogen or lower alkyl and X is halogen; and their physiologically acceptable salts. These compounds have diuretic and hypotensive actions.

Furukawa, et al., in U.S. Pat. No. 4,355,040 issued Oct. 19, 1982, discloses hypotensive imidazole-5-acetic acid derivatives having the formula:

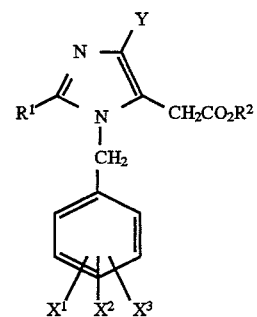

Wherein $R^1$ is lower alkyl, cycloalkyl, or phenyl optionally substituted; $X^1$, $X^2$, and $X^3$ are each hydrogen, halogen, nitro, amino, lower alkyl, lower alkoxy, benzyloxy, or hydroxy; Y is halogen and $R^2$ is hydrogen or lower alkyl; and salts thereof.

Furukawa, et al., in U.S. Pat. No. 4,340,598, issued Jul. 20, 1982, discloses hypotensive imidazole derivatives of the formula:

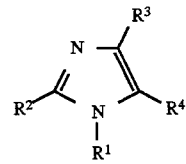

Wherein $R^1$ is lower alkyl or, phenyl $C_{1-2}$ alkyl optionally substituted with halogen or nitro; $R^2$ is lower alkyl, cycloalkyl or phenyl optionally substituted; one of $R^3$ and $R^4$ is —$(CH_2)_nCOR^5$ where $R^5$ is amino, lower alkoxyl or hydroxyl and n is 0, 1, 2 and the other of $R^3$ and $R^4$ is hydrogen or halogen; provided that $R^1$ is lower alkyl or phenethyl when $R^3$ is hydrogen, n=1 and $R^5$ is lower alkoxyl or hydroxyl; and salts thereof.

Furukawa, et al., in European Patent Application 103,647 discloses 4-chloro-2-phenylimidazole-5-acetic acid derivatives useful for treating edema and hypertension of the formula:

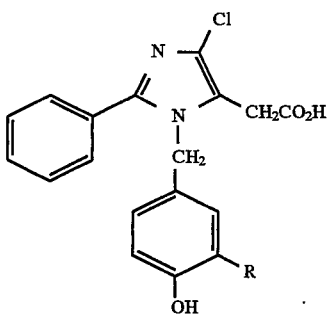

Where R represents lower alkyl and salts thereof.

The metabolism and disposition of hypotensive agent 4-chloro-1-(4-methoxy-3-methylbenzyl)-2-phenyl-imidazole-5-acetic acid is disclosed by H. Torii in *Takeda Kenkyushoho*, 41, No 3/4, 180–191 (1982).

Frazee, et al., in European Patent Application 125,033-A discloses 1-phenyl(alkyl)-2-(alkyl)-thioimidazole derivatives which are inhibitors of dopamine-β-hydroxylase and are useful as antihypertensives, diuretics and cardiotonics.

European Patent Application 146,228 filed Oct. 16, 1984, by S. S. L. Parhi discloses a process for the preparation of 1-substituted-5-hydroxymethyl-2-mercaptoimidazoles.

A number of references disclose 1-benzyl-imidazoles such as U.S. Pat. Nos. 4,448,781 to Cross and Dickinson (issued May 15, 1984); 4,226,878 to Iizuka, et al. (issued Oct. 7, 1980); 3,772,315 to Regel, et al. (issued Nov. 13, 1973); 4,379,927 to Vorbruggen, et al. (issued Apr. 12, 1983); amongst others.

Pals, et al., *Circulation Research*, 29, 673 (1971) describe the introduction of a sarcosine residue in position 1 and alanine in position 8 of the endogenous vasoconstrictor hormone AII to yield an (octa)peptide that blocks the effects of AII on the blood pressure of pithed rats. This analog, [$Sar^1$, $Ala^8$] AII, initially called "P-113" and subsequently "Saralasin," was found to be one of the most potent competitive antagonists of the actions of AII, although, like most of the so-called peptide-AII-antagonists, it also possesses agonistic actions of its own. Saralasin has been demonstrated to lower arterial pressure in mammals and man when the (elevated) pressure is dependent on circulating AII (Pals et. al., *Circulation Research*, 29, 673 (1971); Streeten and Anderson, Handbook of Hypertension, Vol. 5, Clinical Pharmacology of Antihypertensive Drugs, A. E. Doyle (Editor), Elsevier Science Publishers B. V., p. 246 (1984)). However, due to its agonistic character, saralasin generally elicits pressor effects when the pressure is not sustained by AII. Being a peptide, the pharmacological effects to saralasin are relatively short-lasting and are only manifest after parenteral administration, oral doses being ineffective. Although the therapeutic uses of peptide AII-blockers, like saralasin, are severely limited due to their oral ineffectiveness and short duration of action, their major utility is as a pharmaceutical standard.

Currently there are several A II antagonists in development. Among these development candidates, is losartan which is disclosed in a U.S. Pat. No. 5,138,069 issued to DuPont on Aug. 11, 1992. Losartan has been demonstrated to be an orally active A II antagonists, selective for the $AT_1$ receptor subtype.

Some known non-peptide antihypertensive agents act by inhibiting an enzyme, called angiotensin converting enzyme (ACE), which is responsible for conversion of angiotensin I to AII. Such agents are thus referred to as ACE inhibitors, or converting enzyme inhibitors (CEI's). Captopril and enalapril are commercially available CEI's. Based on experimental and clinical evidence, about 40% of hypertensive patients are non-responsive to treatment with CEI's. But when a diuretic such as furosemide or hydrochlorothiazide is given together with a CEI, the blood pressure of the majority of hypertensive patients is effectively normalized. Diuretic treatment converts the non-renin dependent state in regulating blood pressure to a renin-dependent State. Although the imidazoles of this invention act by a different mechanism, i.e., by blocking the AII receptor rather than by inhibiting the angiotensin converting enzyme, both mechanisms involve interference with the renin-angiotensin cascade. A combination of the CEI enalapril maleate and the diruetic hydrochlorothiazide is commercially available under the trademark Vaseretic® from Merck & Co. Publications which relate to the use of diuretics with CEI's to treat hypertension, in either a diuretic-first, stepwise approach or in physical combination, include Keeton, T. K. and Campbell, W. B., Pharmacol. Rev., 31:81 (1981) and Weinberger, M. H., Medical Clinics N. America, 71:979 (1987). Diuretics have also been administered in combination with saralasin to enhance the antihypertensive effect.

Non-steroidal anti-inflammatory drugs (NSAID's) have been reported to induce renal failure in patients with renal under perfusion and high plasma level of AII. (Dunn, M. J., Hospital Practice, 19:99, 1984). Administration of an AII blocking compound of this invention in combination with an NSAID (either stepwise or in physical combination) can prevent such renal failure. Saralasin has been shown to inhibit the renal vasoconstrictor effect of indomethacin and meclofenamate in dogs (Satoh, et at., *Circ. Res.* 36/37 (Suppl. I):I-89, 1975; Blasingham, et al., *Am J. Physiol.* 239:(F360, 1980). The CEI captopril has been demonstrated to reverse the renal vasoconstrictor effect of indomethacin in dogs with non-hypotensive hemorrhage. (Wong, et al., *J. Pharmacol. Exp. Ther.* 219:104, 1980).

DETAILED DESCRIPTION OF THE INVENTION

This invention relates to a novel method of treating atherosclerosis and/or reducing cholesterol alone or in conjunction with the treatment of hypertension using an angiotensin II receptor antagonist.

This invention relates to the use of the angiotensin II receptor antagonists as recited in European patent applications: EP 475,206, EP 497,150, EP 539,086, EP 539,713, EP 535,463, EP 535,465, EP 542,059, EP 497,121, EP 535,420, EP 407,342, EP 415,886, EP 424,317, EP 435,827, EP 433,983, EP 475,898, EP 490,820, EP 528,762, EP 324,377, EP 323,841, EP 420,237, EP 500,297, EP 426,021, EP 480,204, EP 429,257, EP 430,709, EP 434,249, EP 446,062, EP 505,954, EP 524,217, EP 514,197, EP 514,198, EP 514,193, EP 514,192, EP 450,566, EP 468,372, EP 485,929, EP 503,162, EP 533,058, EP 467,207, EP 399,731, EP 399,732, EP 412,848, EP 453,210, EP 456,442, EP 470,794, EP 470,795, EP 495,626, EP 495,627, EP 499,414, EP 499,416, EP 499,415, EP 511,791, EP 516,392, EP 520,723, EP 520,724, EP 539,066, EP 438,869, EP 505,893, EP 530,702, EP 400,835, EP 400,974, EP 401,030, EP 407,102, EP 411,766, EP 409,332, EP 412,594, EP 419,048, EP 480,659, EP 481,614, EP 490,587, EP 467,715, EP 479,479, EP 502,725, EP 503,838, EP 505,098, EP 505,111, EP 513,979, EP 507,594, EP 510,812, EP 511,767, EP 512,675, EP 512,676, EP 512,870, EP 517,357, EP 537,937, EP 534,706, EP 527,534, EP 540,356, EP 461,040, EP 540,039, EP 465,368, EP 498,723, EP 498,722, EP 498,721, EP 515,265, EP 503,785, EP 501,892, EP 519,831, EP 532,410, EP 498,361, EP 432,737, EP 504,888, EP 508,393, EP 508,445, EP 403,159, EP 403,158, EP 425,211, EP 427,463, EP 437,103, EP 481,448, EP 488,532, EP 501,269, EP 500,409, EP 540,400, EP 005,528, EP 028,834, EP 028,833, EP 411,507, EP 425,921, EP 430,300, EP 434,038, EP 442,473, EP 443,568, EP 445,811, EP 459,136, EP 483,683, EP 518,033, EP 520,423, EP 531,876, EP 531,874, EP 392,317, EP 468,470, EP 470,543, EP 502,314, EP 529,253, EP 543,263, EP 540,209, EP 449,699, EP 465,323, EP 521,768, and EP 415,594, which are incorporated by reference into the instant application.

This invention relates to the use of the angiotensin II receptor antagonists as recited in PCT patent applications: WO 92/14468, WO 93/08171, WO 93/08169, WO 91/00277, WO 91/00281, WO 91/14367, WO 92/00067, WO 92/00977, WO 92/20342, WO 93/04045, WO 93/04046, WO 91/15206, WO 92/14714, WO 92/09600, WO 92/16552, WO 93/05025, WO 93/03018, WO 91/07404, WO 92/02508, WO 92/13853, WO 91/19697, WO 91/11909, WO 91/12001, WO 91/11999, WO 91/15209, WO 91/15479, WO 92/20687, WO 92/20662, WO 92/20661, WO 93/01177, WO 91/17771, WO 91/14679, WO 91/13063, WO 92/13564, WO 91/17148, WO 91/18888, WO 91/19715, WO 92/02257, WO 92/04335, WO 92/05161, WO 92/07852, WO 92/15577, WO 93/03033, WO 91/16313, WO 92/00068, WO 92/02510, WO 92/09278, WO 9210179, WO 92/10180, WO 92/10186, WO 92/10181, WO 92/10097, WO 92/10183, WO 92/10182, WO 92/10187, WO 92/10184, WO 92/10188, WO 92/10180, WO 92/10185, WO 92/20651, WO 93/03722, WO 93/06828, WO 93/03040, WO 92/19211, WO 92/22533, WO 92/06081, WO 92/05784, WO 93/00341, WO 92/04343, WO 92/04059, and WO 92/05044, which are incorporated by reference into the instant application.

This invention relates to the use of the angiotensin II receptor antagonists as recited in U.S. Pat. Nos.: 5,104,877, 5,187,168, 5,149,699, 5,185,340, 4,880,804, 5,138,069, 4,916,129, 5,153,197, 5,173,494, 5,137,906, 5,155,126, 5,140,037, 5,137,902, 5,157,026, 5,053,329, 5,132,216, 5,057,522, 5,066,586, 5,089,626, 5,049,565, 5,087,702, 5,124,335, 5,102,880, 5,128,327, 5,151,435, 5,202,322, 5,187,159, 5,198,438, 5,182,288, 5,036,048, 5,140,036, 5,087,634, 5,196,537, 5,153,347, 5,191,086, 5,190,942, 5,177,097, 5,212,177, 5,208,234, 5,208,235, 5,212,195, 5,130,439, 5,045,540, 5,041,152, and 5,210,204, which are incorporated by reference into the instant application.

The method of treating atherosclerosis and/or reducing cholesterol alone or in conjunction with the treatment of hypertension using an angiotensin II receptor antagonist of formula I.

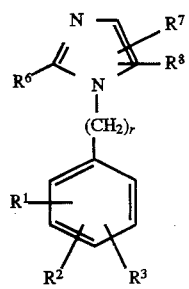

wherein:

$R^1$ is:

-continued

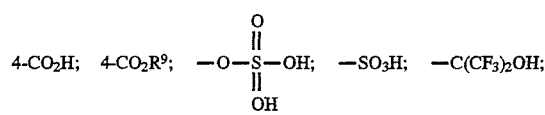

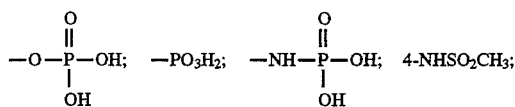

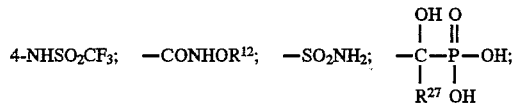

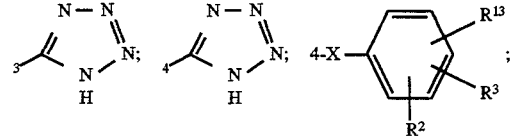

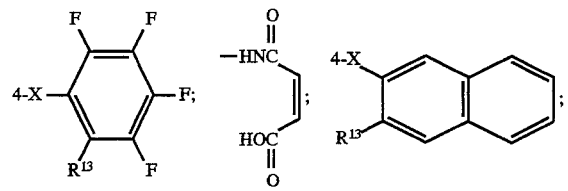

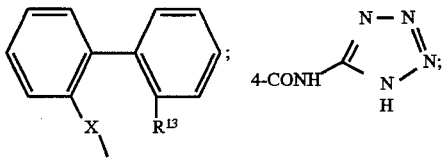

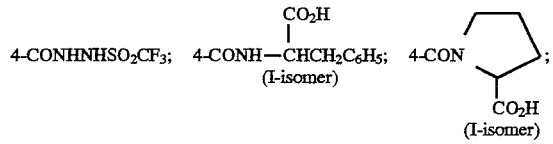

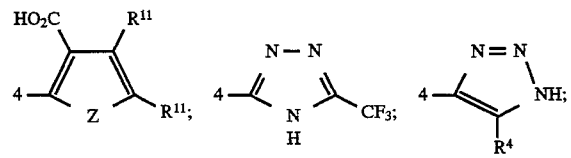

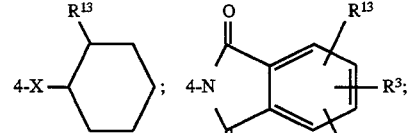

or

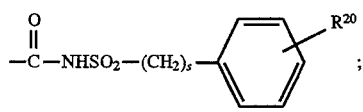

$R^2$ is H; Cl; Br; I; F; $NO_2$; CN; alkyl of 1 to 4 carbon atoms; acyloxy of 1 to 4 carbon atoms; alkoxy of 1 to 4 carbon atoms; $CO_2H$; $CO_2R^9$; $HNSO_2CH_3$; $NHSO_2CF_3$; $CONHOR^{12}$;

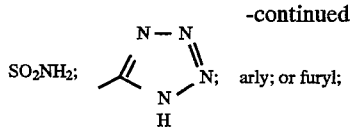 arly; or furyl;

$R^3$ is H; Cl, Br, I or F; alkyl of 1 to 4 carbon atoms or alkoxy of 1 to 4 carbon atoms;

$R^4$ is CN, $NO_2$ or $CO_2R^{11}$;

$R^5$ is H, alkyl of 1 to 6 carbon atoms, cycloalkyl of 3 to 6 carbon atoms alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms, cycloalkylalkyl, of 4 to 10 carbon atoms; cycloalkylalkenyl or cycloalkylalkynyl 5 to 10 carbon atoms; $(CH_2)_sZ(CH_2)_mR^5$ optionally substituted with F or $CO_2R^{14}$; benzyl substituted on the phenyl ring with 1 or 2 halogens, alkoxy of 1 to 4 carbon atoms, alkyl of 1 to 4 carbon atoms or nitro;

$R^7$ is H, F, Cl, Br, I, $NO_2$, $C_vF_{2v+1}$, where v=1–6, $C_6F_5$; CN;

straight or branched alkyl of 1 to 6 carbon atoms; phenyl or phenylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, $CF_3$, and COOR, where R is H, alkyl of 1 to 4 carbon atoms, or phenyl;

$R^8$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; —$(CH_2)_m$-imidazol-1-yl; —$(CH_2)_m$-1,2,3-triazolyl optionally substituted with one or two group selected from $CO_2CH_3$ or alkyl of 1 to 4 carbon atoms; —$(CH_2)_s$ tetrazolyl;

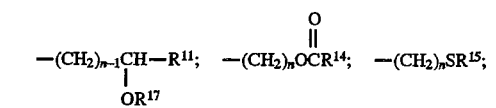

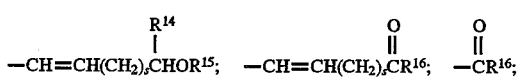

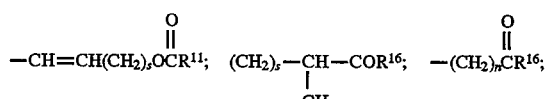

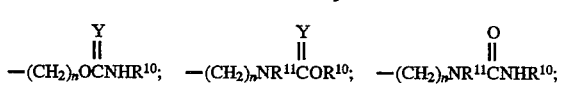

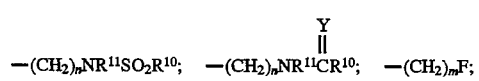

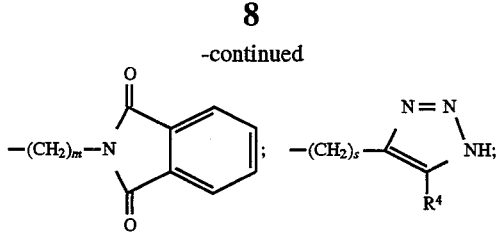

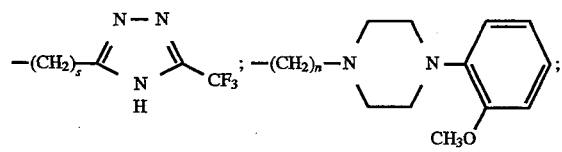

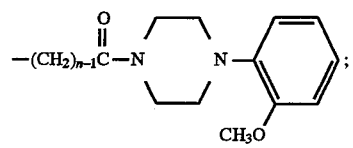

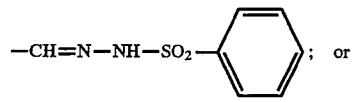

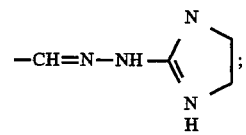

$R^9$ is: —CH(R^{24})—OCR^{21} (=O);

$R^{10}$ is alkyl of 1 to 6 carbon atoms or perfluoroalkyl of 1 to 6 carbon atoms, 1-adamantyl, 1-naphthyl, 1-(1-naphthyl) ethyl, or $(CH_2)_pC_6H_5$;

$R^{11}$ is H, alkyl of 1 to 6 carbon atoms, cycloalkyl of 3 to 6 carbon atoms, phenyl or benzyl;

$R^{12}$ is H, methyl or benzyl;

$R^{13}$ is —$CO_2H$; —$CO_2R^9$; —$CH_2CO_2H$, —$CH_2CO_2R^9$;

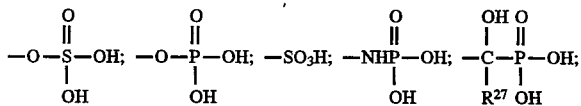

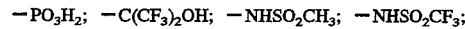

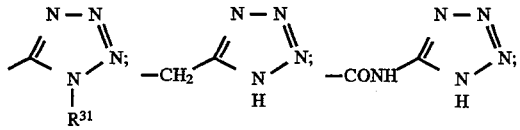

$R^{14}$ is H, alkyl or perfluoroalkyl of 1 to 8 carbon atoms, cycloalkyl of 3 to 6 carbon atoms, phenyl or benzyl;

$R^{15}$ is H, alkyl of 1 to 6 carbon atoms, cycloalkyl of 3 to 6 carbon atoms, phenyl, benzyl, acyl of 1 to 4 carbon atoms, phenacyl;

$R^{16}$ is H, alkyl of 1 to 6 carbon atoms, cycloalkyl of 3 to 6 carbon atoms, $(CH_2)_pC_6H_5$, $OR^{17}$, or $NR^{18}R^{19}$;

$R^{17}$ is H, alkyl of 1 to 6 carbon atoms, cycloalkyl of 3 to 6 carbon atoms, phenyl or benzyl; $R^{18}$ and $R^{19}$ independently are H, alkyl of 1 to 4 carbon atoms, phenyl, benzyl, α-methylbenzyl, or taken together with the nitrogen form a ring of the formula:

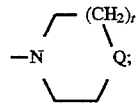

Q is $NR^{20}$, O or $CH_2$;
$R^{20}$ is H, alkyl of 1–4 carbon atoms, or phenyl;
$R^{21}$ is alkyl of 1 to 6 carbon atoms, $-NR^{22}R^{23}$, or

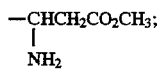

$R^{22}$ and $R^{23}$ independently are H, alkyl of 1 to 6 carbon atoms, benzyl, or are taken together as $(CH_2)_u$, where u is 3–6;
$R^{24}$ is H, $CH_3$ or $-C_6H_5$;
$R^{25}$ is $NR^{27}R^{28}$, $OR^{28}$, $NHCONH_2$, $NHCSNH_2$,

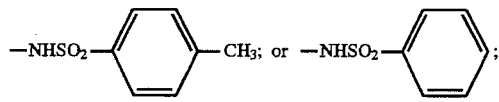

$R^{26}$ is hydrogen, alkyl with from 1 to 6 carbon atoms, benzyl, or allyl;
$R^{27}$ and $R^{28}$ are independently hydrogen, alkyl with from 1 to 5 carbon atoms, or phenyl;
$R^{29}$ and $R^{30}$ are independently alkyl of 1–4 carbon atoms or taken together are $-(CH_2)_q-$;
$R^{31}$ is H, alkyl or 1 to 4 carbon atoms,$-CH_2CH=CH_2$ or $-CH_2C_6H_4R^{32}$;
X is a carbon-carbon single bond, $-CO-$, $-CH_2-$, $-O-$, $-S-$, $-NH-$,

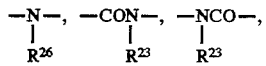

$-OCH_2-$, $-CH_2O-$, $-SCH_2-$, $-CH_2S-$, $-NHC(R^{27})(R^{28})-$, $-NR^{23}SO_2-$, $-SO_2NR^{23}-$, $-CH=CH-$, $-CF=CF-$, $-CH=CF-$, $-CF=CH-$, $-CH_2CH_2-$, $-C(R^{27})(R^{28})NH-$,

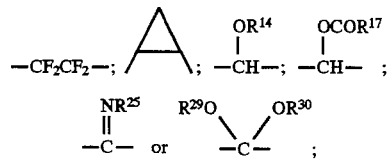

Y is O or S;
Z is O, $NR^{11}$, or S;
m is 1 to 5;
n is 1 to 10;
p is 0 to 3;
q is 2 to 3;
r is 0 to 2;

s is 0 to 5;
t is 0 or 1;
and pharmaceutically acceptable salts of these compounds; provided that:

(1) the $R^1$ group is not in the ortho position;
(2) when $R^1$ is

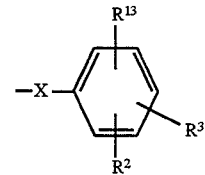

X is a single bond, and $R^{13}$ is $CO_2H$, or

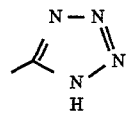

when $R^{13}$ must be in the ortho or meta position; or when $R^1$ and X are as above and $R^{13}$ is $NHSO_2CF_3$ of: $NHSO_2CH_3$, $R^{13}$ must be ortho;

(3) when $R^1$ is

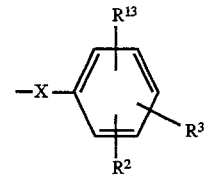

and X is other than a single bond, then $R^{13}$ must be ortho except when $X=NR^{23}CO$ and $R^{13}$ is $NHSO_2CF_3$ or $NHSO_2CH_3$, then $R^{13}$ must be ortho or meta;

(4) when $R^1$ is $4-CO_2H$ or a salt thereof, $R^6$ cannot be S-alkyl;

(5) when $R^1$ is $4-CO_2H$ or a salt thereof; the substituent on the 4-position of the imidazole cannot be $CH_2OH$, $CH_2OCOCH_3$, or $CH_2CO_2H$;

(6) when $R^1$ is

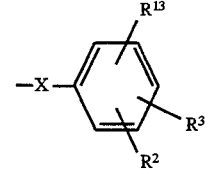

X is $-OCH_2-$, and $R^{13}$ is $2-CO_2H$, and $R^7$ is H then $R^6$ is not $C_2H_5S$;

(7) when $R^1$ is

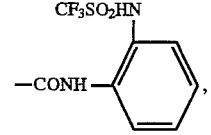

and $R^6$ is n-hexyl then $R^7$ and $R^8$ are not both hydrogen;

(8) when $R^1$ is

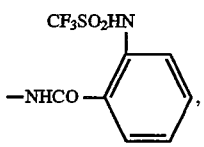

$R^6$ is not methoxybenzyl;

(9) the $R^6$ group

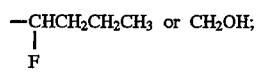

or $CH_2OH$;

(10) when r=0, $R^1$ is

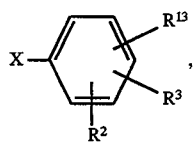

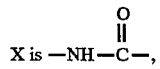

$R^{13}$ is 2-$NHSO_2CF_3$ and $R^6$ is n-propyl, then $R^7$ and $R^8$ are not —$CO_2CH_3$;

(11) when r=0, $R^1$ is

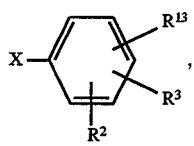

$R^{13}$ is 2-COOH, and $R^6$ is n-propyl, then $R^7$ and $R^8$ are not —$CO_2CH_3$;

(12) when r=1,

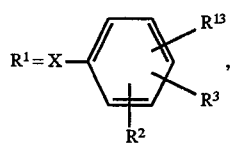

X is a single bond, $R^7$ is Cl, and $R^8$ is —CHO, then $R^{13}$ is not 3-(tetrazol-5-yl);

(13) when r=1,

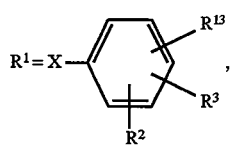

X is a single bond, $R^7$ is Cl, and $R^8$ is —CHO, then $R^{13}$ is not 4-tetrazol-5-yl).

Preferred for their atherosclerotic, anticholesterolemic and antihypertensive activity are the compounds having the formula:

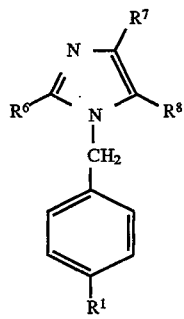

wherein:
$R^1$ is —$CO_2H$; —$NHSO_2CF_3$;

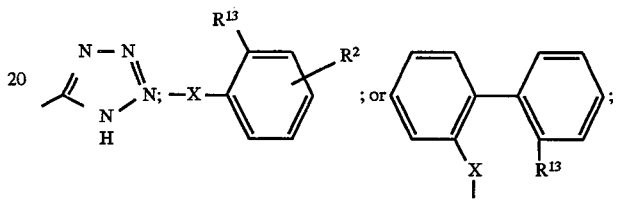

$R^6$ is alkyl of 3 to 10 carbon atoms, alkenyl of 3 to 10 carbon atoms, alkynyl of 3 to 0 carbon atoms, cycloalkyl of 3 to 8 carbon atoms, benzyl substituted on the phenyl ring with up to two groups selected from alkoxy of 1 to 4 carbon atoms, halogen, alkyl of 1 to 4 carbon atoms, and nitro;

$R^8$ is phenylalkenyl wherein the aliphatic portion is 2 to 4 carbon atoms, —$(CH_2)_m$-imidazol-1 yl, —$(CH_2)_m$1, 2,3-triazolyl optionally substituted with one or two groups selected from $CO_2CH_3$ or alkyl of 1 to 4 carbon atoms, $(CH_2)_m$-tetrazolyl, —$(CH_2)_nOR^{11}$;

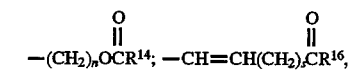

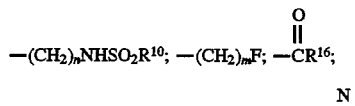

$NHSO_2CF_3$; $SO_3H$;

$R^{16}$ is H, alkyl of 1 to 5 carbon atoms, $OR^{17}$, or $NR^{18}R^{19}$;
X is carbon-carbon single bond,

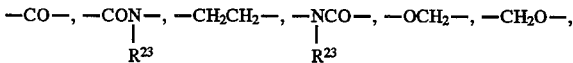

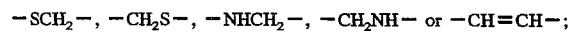

and pharmaceutically acceptable salts of these compounds.

More preferred for the treament of atherosclerosis, anticholestrolemia and hypertension are compounds of the preferred scope wherein:

R² is H, alkyl of 1 to 4 carbon atoms, halogen, or alkoxy of 1 to 4 carbon atoms;

R⁶ is alkyl, alkenyl or alkynyl of 3 to 7 carbon atoms;

R⁷ is H, Cl, Br, $C_vF_{2v+1}$, where v=1–3, or

R⁸ is 

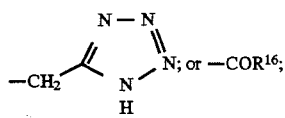

R¹⁰ is CF₃, alkyl of 1 to 6 carbon atoms or phenyl;

R¹¹ is H, or alkyl of 1 to 4 carbon atoms;

R¹³ is CO₂H; CO₂CH₂OCOC(CH₃)₃; NHSO₂CF₃; and

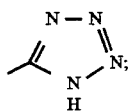

R¹⁴ is H, or alkyl of 1 to 4 carbon atoms;

R¹⁵ is H, alkyl of 1 to 4 carbon atoms, or acyl of 1 to 4 carbon atoms;

R¹⁶ is H, alkyl of 1 to 5 carbon atoms; OR¹⁷; or

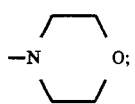

m is 1 to 5;

X is single bond, —O—; —CO—; —NHCO—; or —OCH₂—; and pharmaceutically acceptable salts.

Specifically preferred for their activity in the treatment of atherosclerosis, high cholesterol and hypertension are:

2-Butyl-4-chloro-1-[(2'-(1H-tetrazol-5-yl)biphenyl-4-yl)methyl]-5-(hydroxymethyl)imidazole.

2-Butyl-4-chloro-1-[(2'-carboxybiphenyl-4-yl)methyl]-5-hydroxymethyl) imidazole.

2-Butyl-4-chloro-1-[(2'-carboxybiphenyl-4-yl)methyl]-5-[(methoxycarbonyl) aminomethyl]imidazole.

2-Butyl-4-chloro-1-[(2'-carboxybiphenyl-4-yl)methyl-5-[(propoxycarbonyl) aminomethyl]imidazole.

2-Butyl-4-chloro-1-[(2'-carboxybiphenyl-4-yl)methyl] imidazole-5-carboxaldehyde.

2-Butyl-1-[(2'-carboxybiphenyl-4-yl)methyl]-imidazole-5-carboxaldehyde.

2-(1E-Butenyl)-4-chloro -1-[(2'-carboxybiphenyl -4-yl) methyl]-5-(hydroxymethyl)imidazole.

2-(1E-Butenyl)-4-chloro-1-[(2'-carboxybiphenyl-4-yl) methyl]-imidazole-5-carboxaldehyde.

2-Propyl-4-chloro-1-[(2'-1H-tetrazol-5-yl)biphenyl-4-yl) methyl]-5-(hydroxymethyl) imidazole.

2-Propyl-4-chloro-1 [(2'-1H-tetrazol-5-yl)biphenyl-4-yl) methyl]-imidazole-5-carboxaldehyde.

2-Butyl-4-chloro-1-[2'-1H-tetrazol-5-yl)biphenyl-4-yl) methyl]-imidazole-5-carboxaldehyde.

2-(1E-Butenyl)-4-chloro -1-[(2'-1H-tetrazol -5-yl)biphenyl-4-yl) methyl]-5-hydroxymethyl) imidazole.

2-(1E-Butenyl)-4-chloro-1-[(2'-1H-tetrazol-5-yl)biphenyl-4-yl) methyl]imidazole-5-carboxaldehyde.

2-Butyl -4-chloro -1-[(2'-(1H-tetrazol-5-yl)-biphenyl-4-yl) methyl]-imidazole-5-carboxylic acid.

2-Propyl-4-chloro-1-[(2-'(1H-tetrazol-5-yl)-biphenyl-4-yl) methyl]-imidazole-5-carboxylic acid.

2-Propyl-4-trifluoromethyl-1-[(2'-1H-tetrazol-5-yl) biphenyl-4-yl) methyl]imidazole-5-carboxylic acid.

2-Propyl-4-trifluoromethyl-1-[(2'-1H-tetrazol-5-yl) biphenyl-4-yl) methyl]-5-hydroxylmethyl)imidazole.

2-Butyl-4-trifluoromethyl-1-[(2'-1H-tetrazol -5-yl)biphenyl-4-yl) methyl]imidazole-5-carboxylic acid.

2-Propyl-4-trifluoromethyl-1-[(2'-carboxybiphenyl -4-yl) methyl]-imidazole-5-carboxaldehyde.

2-Propyl-4-pentafluoroethyl-1-[(2'-1H-tetrazol 1–5-yl ) biphenyl-4-yl) methyl]-5-hydroxymethyl)imidazole.

2-Propyl-1-[(2-1H-tetrazol-5-yl)biphenyl-4-yl)methyl] imidazole-4,5-dicarboxylic acid.

2-Propyl-4-pentafluoroethyl-1-[(2'-1H-tetrazol-5-yl) biphenyl-4-yl) methyl]imidazole-5-carboxylic acid.

2-Propyl-4-pentafluoroethyl-[(2'-1H-tetrazol-5-yl)biphenyl-4-yl) methyl]imidazole-5-carboxaldehyde, or a pharmaceutically acceptable salt thereof.

The most preferred angiotensin II receptor antagonist compounds for the treatment of atherosclerosis and/or high cholesterol alone or in conjunction with hypertension are:

2-Butyl-4-chloro-1-[(2'-tetrazol-5-yl)biphenyl-4-yl]methyl] -5-hydroxymethyl) imidazole; and 2-Butyl-4-chloro-1-[(2'-tetrazol-5-yl)biphenyl-4-yl] methylimidazole-5-carboxylic acid or a pharmaceutically acceptable salt thereof.

Note that throughout the text when an alkyl substituent is mentioned, the normal alkyl structure is meant (i.e., butyl is n-butyl) unless otherwise specified.

The angiotensin II antagonist compounds of the present invention can be administered in combination with an HMG-Co A reductase inhibitor for the treatment of atherosclerosis and/or to lower cholesterol. The HMG-Co A reductase inhibitors which are used in this combination therapy, include the compounds represented by the following structural formula (II):

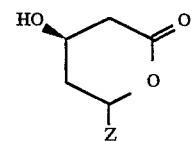

wherein:

Z is selected from:

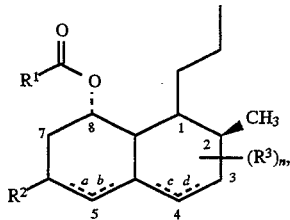

wherein

R¹ is $C_{1-10}$alkyl,

R² is selected from the group consisting of: hydrogen, $C_{1-3}$ alkyl, hydroxy, and $C_{1-3}$ alkyl substituted with hydroxy;

R² is selected from the group consisting of: $C_{1-3}$ alkyl, hydroxy, oxo, and $C_{1-3}$ alkyl substituted with hydroxy;

n is 0,1, or 2;

a, b, c and d are all single bonds or a and c are double bonds or b and d are double bonds or one of a, b, c or d is a double bond;

(b) 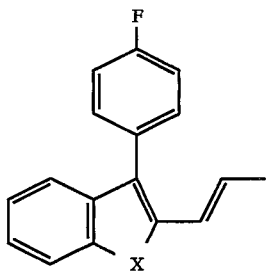

wherein X is $NCH(CH_3)_2$ or $C(CH_2)_4$;

(c) 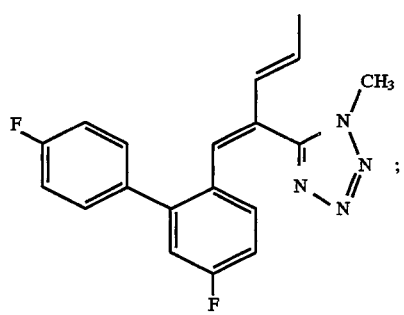

(d) 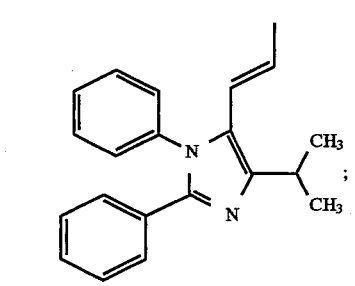

(e) 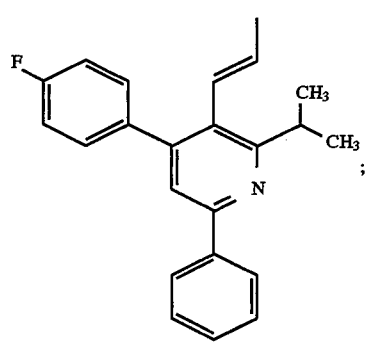

(f) 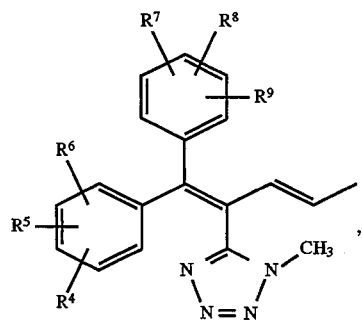

wherein:

$R^4$ and $R^9$ are each independently selected from hydrogen, halogen, $C_{1-4}$ alkyl, $C_{1-4}$ alkoxy and trifluoromethyl, and $R^5$, $R^6$, $R^7$, and $R^8$ are each independently selected from hydrogen, halogen, $C_{1-4}$ alkyl, and $C_{1-4}$ alkoxy;

and corresponding open-ring dihydroxy acid forms of formula III:

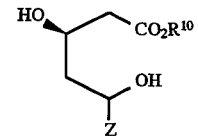

wherein:

$R^{10}$ is selected from from the group consisting of: hydrogen, $C_{1-5}$alkyl, substituted $C_{1-5}$alkyl in which the substituent is selected from the group consisting of: phenyl, dimethylamino, acetylamino, and 2,3-dihydroxypropyl and pharmaceutically acceptable salts;

and pharmaceutically acceptable salts and esters thereof; provided that when when $R^1$ is 1-methylpropyl or 1,1-dimethylpropyl, $R^3$ is hydrogen and b and d represent double bonds and $R^2$ is not methyl.

The terms "halo" and "halogen" each refer to —F, —Cl, —Br and —I.

The term "open-ring dihydroxy acid form and pharmaceutically acceptable salts, and esters" of the compound of formula II refers to the corresponding compound of formula III below:

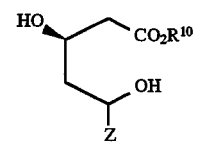

wherein $R^{10}$ is selected from from the group consisting of: hydrogen, $C_{1-5}$alkyl, substituted $C_{1-5}$alkyl in which the substituent is selected from the group consisting of: phenyl, dimethylamino, acetylamino, and 2,3-dihydroxypropyl;

and pharmaceutically acceptable salts thereof.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline N,N'-dibenzylethylenediamine, chloroprocaine, diethanolamine, procaine, N-benzylphenethyolamine, diethylamine, piperazine, tris (hydroxymethyl)aminomethane, and tetramethyl ammonium hydroxide. These salts are prepared by standard procedures.

One class of HMG-Co A reductase inhibitor compounds are those wherein Z is:

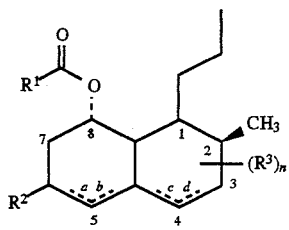

and n is 1.

One subclass of these compounds is where $R^3$ is 5-OH, and a, b, c, and d are each single bonds.

Another subclass of compounds is characterized by $R^3$ being 3-oxo and either a and c are double bonds and b and d are single bonds, or c is a double bond and a, b, and d are single bonds.

Yet a third subclass of these compounds is where $R^3$ is 7-(1-hydroxyethyl), h and d are double bonds; provided that when $R^2$ is OH, either b and d are double bonds and a, and c are single bonds, or c is a double bond and a, b, and d are single bonds, or a, b, c, and d are single bonds.

Representative compounds of this class are: lovastatin, simvastatin and pravastatin:

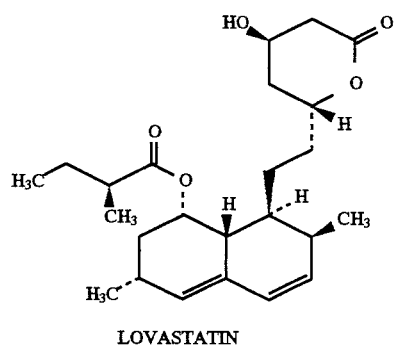

LOVASTATIN

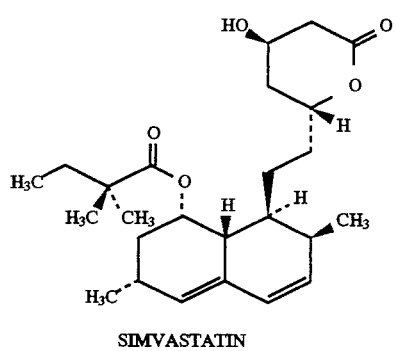

SIMVASTATIN

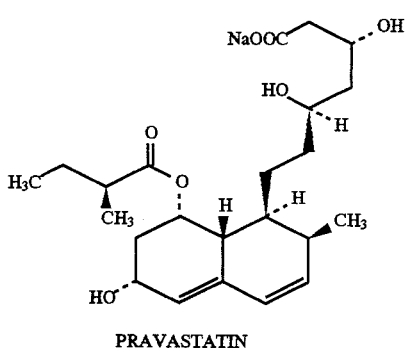

PRAVASTATIN

Another class of HMG-Co A reductase inhibitor compounds are those wherein Z is:

(a)

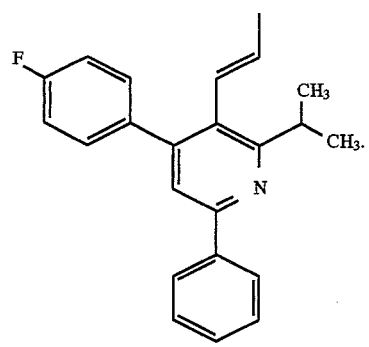

A method of treatment for atheroscelerosis and/or to lower cholesterol administering a combination of an angiotensin II antagonist compound, an HMG-Co A reductase inhibitor and an angiotensin converting enzyme inhibitor. An embodiment of the ACE inhibitors useful in this method of treatment are enalapril and lisinopril.

Pharmaceutically suitable salts include both the metallic (inorganic) salts and organic salts; a list of which is given in Remington's Pharmaceutical Sciences, 17th Edition, pg. 1418 (1985). It is well known to one skilled in the art that an appropriate salt form is chosen based on physical and chemical stability, flowability, hydroscopicity and solubility. Preferred salts of this invention for the reasons cited above include potassium, sodium, calcium and ammonium salts.

Also within the scope of this invention is a method of treatment of atheroscelerosis, high cholesterol and hypertension using pharmaceutical compositions comprising a suitable pharmaceutical carrier and a compound of Formula (I). The pharmaceutical compositions which contain one or more other therapeutic agents, such as a diuretic or a non-steroidal anti-inflammatory drug.

It should be noted in the foregoing structural formula, when a radical can be a substituent more than one previously defined radical, that first radical can be selected independently in each previously defined radical. For example, $R^1$, $R^2$ and $R^3$ can each be $CONHOR^{12}$. $R^{12}$ need not be the same substituent in each of $R^1$, $R^2$ and $R^3$ but can be selected independently for each of them.

SYNTHESIS

The novel compounds of Formula (I) may be prepared using the reactions and techniques described in U.S. Pat. No. 5,138,069 and WO 93/10106 or one of its three U.S. counterparts, U.S. Pat. No. 5,130,439 issued Jul. 14, 1992, U.S. Pat No. 5,206,374 issued Apr. 27, 1993, and U.S. Ser. No. 07/911,813 filed Jul. 10, 1992.

EXAMPLE 1

2-n-butyl-4-chloro-5-hydroxymethyl-1-[(2'-1H-tetrazol-5-yl)biphenyl-4-yl)methyl]imidazole [DuP-753]

Step A: Preparation of 4'-methylbiphenyl-2-carboxylic acid

Methyl 4'-methylbiphenyl-2-carboxylate (10.0 g, 44.2 mmol, 1 eq), 0.5N KOH in methanol (265.5 mL, 133 mmol, 3 eq), and water (50 mL) were mixed and refluxed under $N_2$. After 5 hours, the solvent was removed in vacuo and water (200 mL) and ethyl acetate (200 mL) added. The aqueous layer was acidified with concentrated hydrochloric acid to a pH of 3 and the layers were separated. The aqueous phase was extracted with ethyl acetate (2×200 mL), the organic layers collected, dried (MgSO₄) and the solvent removed in vacuo to yield 8.71 g of a white solid; m.p. 140.0°–145.0°. NMR (200 MHz, DMSO-d₆) δ 7.72 (d, 1H, J=7 Hz); 7.56 (t, 1H, J=7 Hz); 7.45 (d, 1H, J=7 Hz); 7.40 (t, 1H, I=7 Hz); 7.25 (s, 4H); 2.36 (s, 3H). Anal Calcd. for $C_{14}H_{12}O_2$: C, 79.23; H, 5.70. Found: C, 79.22; H, 5.47.

Step B: Preparation of 4'-Methyl-2-cyanobiphenyl

4'-Methylbiphenyl-2-carboxylic acid (8.71 g, 41 mmol, 1 eq) and thionyl chloride (30.0 mL, 411 mmol, 10 eq) were mixed and refluxed for 2 hours. The excess thionyl chloride was removed in vacuo and the residue was taken up in toluene. The toluene was removed by rotary evaporation and this toluene evaporation procedure was repeated to ensure that all of the thionyl chloride was removed. The crude acid chloride was then added slowly to cold (0° C.) concentrated $NH_4OH$ (50 mL) so that the temperature was kept below 15°. After 15 minutes of stirring, water (100 mL) was added and solids precipitated. These were collected, washed well with water and dried under high vacuum over $P_2O_5$ in a dessicator overnight to yield 7.45 g of white solid; m.p. 126.0°–128.5°. NMR (200 MHz, DMSO-d₆) δ 7.65–7.14 (m, 10H), 2.32 (s, 3H). Anal Calcd. for $C_{14}H_{13}NO$: C, 79.59; H, 6.20; N, 6.63. Found C, 79.29; H, 6.09; N, 6.52.

The above product amide (7.45 g, 35 mmol, 1 eq) and thionyl chloride (25.7 ml., 353 mmol, 10 eq) were mixed and refluxed for 3 hours. The thionyl chloride was removed using the same procedure as described above. The residue was washed with a little hexane which partly solubilized the product, but removed the impurity as well to yield 6.64 g of white solid; m.p. 44.0°–47.0°. NMR (200 MHz, DMSO-d₆) δ 7.95 (d, 1H, J=8 Hz); 7.78 (t, 1H, J=7 Hz); 7.69–7.32 (m, 6H); 2.39 (s, 3H). Anal Calcd. for $C_{14}H_{11}N$: C, 87.01; H, 5.74. Found C, 86.44; H, 5.88.

Step C: Preparation of 4'-bromomethyl-2-cyanobiphenyl

A solution of 5.59 g of 4'-methyl-2-cyanobiphenyl, 29 mmol of N-bromosuccinimide, 0.9 mmol of benzoylperoxide and 500 mL of carbon tetrachloride was reflexed for 3 hours. After cooling to room temperature, the resulting suspension was filtered and then concentrated in vacuo to provide the crude 4'-bromomethyl-2-cyanobiphenyl. The product was recrystallized from ether to yield 4.7 g of product; m.p. 114.5°–120.0°. NMR (200 MHz, CDCl₃) δ 7.82–7.37 (m, 8H); 4.50 (s, 2H). Anal. Calcd. for $C_{14}H_{10}BrN$: C, 61.79, H, 3.70; N, 5.15. Found: C, 62.15; H, 3.45; N, 4.98.

Step D: Preparation of 2-n-butyl-4-chloro-1-[2'-cyanobiphenyl-4-yl) methyl]-5-hydroxymethyl)-imidazole To a suspension of 1.43 g of sodium methoxide in 20 mL of dimethylformamide at 25° was added a solution of 15.3 mmol of 2-butyl- 4(5)-chloro-5(4)-hydroxymethyl imidazole (prepared as described in U.S. Pat. No. 4,355,040) in 15 mL of DMF. The resulting mixture was stirred at 25° for 0.25 hours, and then to this mixture 4.6 g, 16.9 mmol of 4'bromomethyl-2-cyanobiphenyl in 15 mL of DMF. Finally, the reaction mixture was stirred at 40° for 4 hours. After cooling to 25°, the solvent was removed in vacuo. The residue was dissolved in 1: 1 hexane/ethyl acetate, and this solution was washed with water and brine, dried over anhydrous sodium surf ate, filtered, and concentrated. The crude product contains two regioisomers, the faster moving one by TLC being the more potent isomer. Flash chromatography in 1:1 hexane/ethyl acetate over silica gel to separate the regioisomeric products yielded 2.53 g of the faster eluting isomer. Recrystallization from acetonitrile yielded 1.57 g of analytically pure product; m.p. 153.5°–155.5°. NMR (200 MHz, CDCl₃) δ 7.82–7.43 (m, 6); 7.12 (d, 2, J=8 Hz); 5.32 (s, 2); 4.52 (s, 2); 2.62 (t, 2, J=7 Hz); 1.70 (t of t, 2, J=7.7 Hz); 1.39 (t of q, 2, J=7,7 Hz); 0.90 (t, 3, J=7 Hz). Anal. Calcd. for $C_{22}H_{22}ClN_3O$: C, 69.56; H, 5.84; N, 11.06. Found: C, 69.45; H, 5.89; N, 10.79.

Step E: Preparation of 2-n-butyl-4-chloro-5-hydroxymethyl-1-[(2'-(1H-tetrazol-5-yl)biphenyl-4-yl)methyl]imidazole 2-n-Butyl-4-chloro-1-[(2'-cyanobiphenyl-4-yl)-methyl]-5-(hydroxymethyl) imidazole (11.93 g, 1.0 eq), sodium azide (3 eq), and ammonium chloride (3 eq) were mixed and stirred in DMF (150 mL) in a round bottom connected to a reflux condenser under $N_2$. An oil bath with a temperature controller was then used to heat the reaction at 100° C. for 2 days, after which the temperature was raised to 120° C., for 6 days. The reation was cooled and 3 more equivalents of ammounium chloride and sodium azide were added. The reaction was again heated for 5 more days at 120° C. The reaction was cooled, the inorganic salts filtered, and the filtrate solvent removed in vacuo. Water (200 mL) and ethyl acetate (200 mL) were added to the residue and the layers were separated. The aqueous layer was extracted with ehtyl acetate (2×200 mL), the organic layers were collected, dried (MgSO₄) and the solvent removed in vacuo, to yield a dark yellow oil. The product was purified by flash chromatography in 100% ethyl acetate to 100% ethanol over silica gel to yield 5.60 g of a light yellow solid. Recrystallization from acetonitrile yielded 4.36 g of light yellow crystals which still melted broadly. The crystals were taken up in 100 mL of hot acetonitrile. The solid that did not dissolve was filtered off to yield 1.04 g of product as a light yellow solid; m.p. 183.5°–184.5°. Upon cooling, the mother liquor yielded an additional 1.03 g of product as a light yellow solid; m.p. 179.0°–180.0°. NMR (200 MHz, DMSO-d₆) δ 7.75–7.48 (m, 4H); 7.07 (d, 2H, J=9 Hz); 7.04 (d, 2H, I=9 Hz); 5.24 (s, 2H); 5.24 (bs, 1H); 4.34 (s, 2H); 2.48 (t, 2H, J=7 Hz); 1.48 (t of t, 2H, J=7,7 Hz); 1.27 (t of q, 2H, J=7,7 Hz); 0.81 (t, 3H, J=7 Hz). Anal. Calcd. for $C_{22}H_{23}ClN_6O$: C, 62.48; H, 5.48; Cl, 8.38. Found for the solids which did not dissolve in 100 mL of acetonitrile: C, 62.73; H, 5.50; Cl, 8.26. Found for the solids obtained from the mother liquor: C, 62.40; H, 5.23; Cl, 8.35.

EXAMPLE 2

2-butyl-1-[2'-1H-tetrazol-5-yl)-biphenyl-4-yl) methyl]-4-chloroimidazole-5—Carboxylic acid (EXP-3174)

A mixture of 2-butyl-5-hydroxymethyl-4-chloro-1-[2'-triphenylmethyltetrazol-5-yl)-biphenyl-4-yl)methyl] imidazole and activated manganese dioxide in 50 mL of methylene chloride was stirred at 25° C. At 24 hours into the reaction 2.00 g of manganese dioxide was added. After a total of 100 hours the reaction mixture was filtered with methylene chloride. The solids then were washed with methanol, and the methanol filtrate concentrated. The residue was dissolved in water. The resulting aqueous solution was adjusted to pH 3 using 10% hydrochloric acid and then extracted with 4:1 chloroform/i-propanol. The combined organic phases were washed with brine, dried over anhydrous sodium sulfate, filtered, and concentrated. Column chromatography (elution(95:5:0.5 chloroform/methanol/acetic acid) furnished 2-butyl-1-[(2'-1H-tetrazol-5-yl)-biphenyl-4-yl)methyl]-4-chloroimidazole-5-carboxylic acid as an amorphous solid. NMR (200 MHz, DMSO-d₆): δ 7.46–7.63 (m, 4H), 7.05 (d, 2H, J=8 Hz), 6.93 (d, 2H, J=8Hz), 5.56 (s, 2H), 4.10 (s, 12H), 2.55 (t, 2H, J=7.5 Hz), 1.44–1.52 (m, 2H), 1.17–1.28 (m, 2H), 0.78 (t, 3H, J=7 Hz).

EXAMPLE 3

2-n-Butyl-4-chloro-1-[(2'-2-triphenylmethyl-2H-tetrazol-5-yl)-1,1'-biphenyl-4-yl)methyl]-1H-imidazole-5-methanol Step A: 2-(2'-Triphenylmethyl-2'H-tetrazol-5'-yl) phenylboronic acid Alternative 1

To a 22 L flask under nitrogen purge was charged 8.25 L acetone, followed by 1.1 kg 5-phenyltetrazole. Triethylamine (800 g) was added in such a rate that the temperature was maintained below 35° C. with some cooling. Solid trityl chloride was charged to this light suspension in five 440 g portions. The temperature was maintained below 35° C. An additional 1.38 L acetone was added to the reaction which was then maintained at 25° to 30° C. with stirring for 2 hours. Water (2.2 L) was added and the mixture was chilled to 15° to 20° C. The solid was collected by filtration; the filter cake was rinsed with 1.65 L 50% acetone-water followed by excess amount of water. The wet cake was re-slurried in 8 L acetone and 8 L of water was added slowly. The suspension was stirred for 1 hour then filtered. The filter cake was rinsed with 3 to 5 L of water. The white solid was dried in a vacuum oven at 40°–45° C. to a constant weight of 3.0 kg, mp 158°–160° C.

To a dry 12 L flask under nitrogen purge was charged 3.19 L of dry tetrahydrofuran (THF). With agitation, 398 g of 5-phenyl-2-trityl-tetrazole prepared above was charged. The system was evacuated and released to nitrogen three times and then cooled to −20° C. A solution of butyl lithium in heptane (1.6M, 477 g) was then added to the reaction mixture while maintaining the temperature at −15° C. to −20° C. The resultant deep red solution was stirred at −15° C. for 1 hour during which time the lithium salt crystallized out. The solid suspension was cooled to −25° C. again 333 g triisopropylborate was charged at a temperature range of −20° to −25° C. After the addition, the mixture was allowed to warm to 20° C. without heating. About 2.5 L of solvent was removed by vacuum distillation. The pot temperature was kept below 40° C. To the mixture was then added 2.66 L of 3% acetic acid in water and the resultant suspension was stirred for 1 hour. The white solid was collected by filtration. The solid cake was rinsed with 1.5 L of 20% tetrahydrofuran in water, followed by 3 L of water. The solid was dried under vacuum at room temperature to a constant weight of 502.3 g, mp 142°–146° C. (dec.).

Alternative 2

A preferred alternative procedure for preparing the title compound of this Example 1 is by means of the following procedure.

5-Phenyltetrazole (14.6 g, 100 mmol was suspended in dry THF (120 ml) under nitrogen and triethylamine (14.8 ml, 105 mmol) was added while maintaining the temperature at 15° to 20° C. Triphenylchloromethane (29.3 g, 105 mmol) in dry THF (60 ml) was then added slowly to the mixture at ≦25° C. After the addition was complete the mixture was warmed to 35° C. for 1 hour and then cooled at 0° C. for 1 hour. The precipitated triethylammonium chloride was filtered and the filtrate was degassed via vacuum/nitrogen purges (3×). The degassed solution was cooled to −20° C. and butyllithium (1.6M in hexanes) was added until a pink color persisted for 2 minutes. The pink color indicated that the solution was completely dry. More butyllithium (65.6 ml, 105 mmol) was charged at ≦−15° C. The deep red heterogeneous mixture was aged at −20° to −15° C. for 1 hour and triisopropylborate (30.6 ml, 130 mmol) was added while maintaining the temperature at ≦−15° C.

The deep red solution was aged at −15° C. for 30 minutes and then warmed to 10° C. over 1 hour. The mixture volume was reduced by ~200 ml in vacuo at ≦15° C. at which time <5% of hexanes (vs THF) remained. The residue was diluted with THF to a total volume of 160 ml and isopropanol (60 ml) was added. The solution was cooled to 0° C. and saturated aqueous ammonium choride (40 ml, 200 mmol) was charged within 15 minutes. The mixture was aged at 20° to 25° C. for 30 minutes and water (100 ml) was added over 30 to 45 minutes. After aging the mixture for 1 hour, the crystallized product was collected by filtration and washed with cold 80% aqueous isopropanol. The filter cake was air dried on the filter to give 69.7 g (86% yield, corrected for 82% purity) of product as the THF mono-solvate.

Step B: 2-n-butyl-4-chloro-5-hydroxymethyl-1-p-bromobenzyl-1H-imidazole

A suspension of 2-n-butyl-4-chloro-1H-imdazole-5-carboxyaldehyde (146.9 g, 0.78 tool) and p-bromobenzyl bromide (195 g, 0.78 mol) in dimethylacetamide (1.0 L) was cooled to 0° C. and potassium carbonate (1.38 g, 1.0 tool) was added. The mixture was aged for three hours at 0° C. and then at 20° to 25° C. or two to four hours. The mixture was diluted with dimethylacetamide (0.15 L) and then filtered. The filter cake was washed with dimethylacetamide (50 ml). The combined filtrates were diluted with methanol (0.66 L) and cooled to 0° C. Sodium borohydride (37.8 g, 1.0 mol) was added as a solid and the mixture was aged with stirring at 20° to 25° C. for two hours. Water (1.56 L) was added slowly to crystallize the product. The filter cake was washed carefully with water (1.56 L) and dried in vacuo at 60° C. The yield was 255 g (91%, corrected for 99.5% purity).

Step C: 2-n-butyl-4-chloro-1-[(2'-2-triphenylmethyl-2H-tetrazol-5-yl-1,1'-biphenyl-4-yl)methyl]1H-imidazole-5-methanol All operations described for this example were performed under an atmosphere of nitrogen.

Catalyst Preparation

To a mixture of palladium chloride (10.6 mg) and triphenylphosphine (31.5 mg) was added anhydrous toluene (4 ml). The heterogeneous solution was degassed by vacuum/nitrogen purges (3×) and then heated to 60° C. for 30 minutes. Triisopropylphosphite (30.0 microliters) was added and the mixture was further heated at 60° C. until a homogeneous solution was obtained (1 to 2 hours).

Coupling 2-(2'-triphenylmethyl -2'H-tetrazol -5'-yl)phenylboronic acid of Example 3, Step A (1.3 g) was suspended in toluene (4 ml) and water (100 microliters) was added. The heterogeneous mixture was stirred at room temperature for 30 minutes and potassium carbonate (0.7 g) was then charged followed by the titled product of Example 3, Step B (0.7 g). The mixture was degassed via vacuum/nitrogen purges (3×) and the above catalyst solution was added. The temperature of the mixture was raised 80° to 85° C. and kept at this temperature for 2 hours. After the mixture was cooled to 40° C., water (5 ml) was added. The aqueous layer was removed and the organic phase was concentrated in vacuo at ≦30° C. to a volume of ~3 ml. Methyl i-butyl ketone (MIBK) (8 ml) was added and the mixture was again reduced to ~3 ml. The mixture was diluted with MIBK (4 ml) and water (36 microliters), heated to 60° C. and then cooled and aged first at 0° C. for 30 minutes followed by aging at −10° C. with stirring for 2 hours. The crystallized product was collected by filtration as a mono-MIBK solvate (1.44 g, 94% yield). The crude product was dissolved in MIBK (2.1 ml) at 80° C., the solution was filtered hot at 80° C. and water (33.8 microliters) was added. The solution was cooled slowly to 0° C. over 1 hour and aged at 0° C. for 30 minutes followed by aging at −10° C. with stirring for 2 hours. After filtration 1.38 g of the mono-MIBK solvated product was recovered (90% yield).

EXAMPLE 4

2-n-Butyl-4-chloro -1-[(2'-2-triphenylmethyl -2H-tetrazol -5-yl)-1,1'-biphenyl-4-methyl]-1H-imidazole-5-methanol All operations described for this example were performed under an atmosphere of nitrogen.

Step A: Catalyst Preparation

The following two procedures can be used with similar results.

Alternative Procedure 1

To a mixture of palladium chloride (354 mg) and triphenylphosphine (2.1 g) was added anhydrous tetrahydrofuran (THF) (75 ml). The heterogeneous solution was degassed by vacuum/nitrogen purges (3×) and then refluxed for 4 hours.

Most of the palladium chloride changed over to bis (triphenylphosphine) palladium chloride during the reflux. Some insoluble black solids were still observed at this point.

The heterogeneous THF solution containing the phosphinated palladium chloride was cooled to room temperature and diethylzinc (4.0 ml, 1M in hexanes) was added. Except for a small mount of black solids, the solution essentially became homogeneous after stirring for 30 minutes. This activated catalyst solution was used in the coupling step described below.

Alternative Procedure 2

To a mixture of palladium chloride (354 mg) and triphenylphosphine (2.1 g) was added anhydrous THF (75 ml). The heterogeneous solution was degassed by vacuum/nitrogen purges (3×) and then triisopropylphosphite (0.99 ml) was added. The mixture was maintained at room temperature until all the palladium chloride was dissolved and a homogeneous solution was obtained (0.5 to 1 hour).

Step B: Benzyltrimethylammonium Carbonate Preparation

To a benzyltrimethylammonium hydroxide solution (42 g) was added ammonium carbonate (5.0 g) and the reaction was aged with stirring until all of the ammonium carbonate dissolved (~30 minutes). The methanol solvent was removed in vacuo and further displaced with THF (3×10 ml). The residual carbonate was dissolved in THF (90 ml).

Step C: Coupling Step

To the carbonate solution prepared in Example 4, Step B was charged the titled product of Example 3 (24.0 g) and the titled product of Example 3, Step B (14.2 g). The mixture was degassed by vacuum/nitrogen purges (5×), followed by the addition of the catalyst solution prepared as recited in Example 4, Step A (procedure 1 or 2),. The reaction mixture was heated to reflux, aged until completion (8 to 10 hours), cooled to room temperature and filtered through a pad Celite. The Celite was further washed with THF (3×10 ml). The yield was 89 wt %.

EXAMPLE 5

2-n-Butyl-4-chloro -1-[(2'-(tetrazol-5-yl)-1,1'-biphenyl-4-yl)methyl]-1H-imidazole-5-methanol potassium salt 2-n-butyl-4-chloro -1-[(2'-2-triphenylmethyl-2H-tetrazol -5-yl)-1,1'-biphenyl-4-yl)methyl]-1H-imidazole-5-methanol, obtained from Example 3 or 4, (5.0 g, 6.54 mmol) was dissolved in THF (60 ml). 4N Sulfuric acid (38 ml, 152 mmol) was added with stirring at 25° to 30° C. The solution was aged overnight at 20° to 25° C. and isopropyl acetate (60 ml) was then added. The layers were separated and the organic phase was back-extracted with 4N sulfuric acid (19 ml). The aqueous layers were combined and the organic solvents (THF and isopropyl acetate) were removed in vacuo. The remaining aqueous solution was diluted with THF (10% of THF by volume) and passed through a pad of Ecosorb S 402 (5.0 g). The pad was rinsed with 10% THF in 4 N sulfuric acid. The filtrate was then passed through a column of SP-207 (60 ml) and the column was washed with water (180 ml) followed with 1M $K_2HPO_4$ (180 ml). The pH of the eluent was monitored to ensure complete potassium salt formation. Further washing with water (180 ml) removed the surf ate and excess phosphate. The potassium salt product was eluted with 20% aqueous THF. Concentration of the aqueous solution and dilution with isopropanol gave crystalline product. Attentively, the product was isolated by spray drying. The yield was 2.56 g (85%).

EXAMPLE 6

1-Bromo-4-2'-n-butyl-4'-chloro-5'-hydroxymethylimidazole-1'H-1'-yl) methylbenzene Step A: Alkylation To 200 mL of dimethyl acetamide under a nitrogen atmosphere in a 1-liter 3-necked flask fitted with a mechanical stirrer and thermocouple is charged 30.8 g (0.163 mol) of 2-n-butyl-4-chloro-5-formyl-1H-imidazole and 43.7 g (0.16 mol) of 4-bromobenzyl bromide. The solution is cooled to −5° C. followed by portionwise addition of 27.1 g (0.19 mol) of powdered potassium carbonate over 10 min with rapid stirring while keeping the reaction temperature between −5°–0° C. The slurry is stirred at −5° C. for 2 h and room temperature for 2 h or until the alkylation is complete.

Step B: Filtration

The slurry is filtered and the cake is washed with an anhydrous mixture of dimethyl acetamide (30 mL) and methanol (130 mL). The filtrate is used directly in the next step.

Step C: Reduction

Under a nitrogen atmosphere, 1.85 g (48 mmol) of powdered sodium borohydride is added portionwise over 0.5 h to the filtrate at −15° C. in a 5-liter 3-necked flask with a mechanical stirrer and a thermocouple, keeping the reaction temperature between −15° to −5° C. The mixture is warmed to room temperature and aged for 1 h or until the reduction is complete.

Step D: Crystallization

Acetic acid (2.74 mL) is added dropwise over 10 min with rapid stirring while keeping the temperature of the mixture at 20°–25° C. This mixture is aged at room temperature for 0.5 h, followed by the addition of water (160 mL) dropwise over ·1 h. The solution is seeded with imidazole 4 and followed by the addition of water (166 mL) dropwise over 1 h. The product precipitated within 0.5 h. The slurry is aged at room temperature for 2 h, cooled to 10° C., aged for 0.5 h and the solid is filtered. The cake is washed with 320 mL of water, suction dried under nitrogen at room temperature for 2 h and oven dried under house vacuum (−24 psi) at ≦60° C. for 12 h to afford 54.3 g of 1-bromo-4-(2'-n-butyl-4'-chloro -5'-hydroxymethylimidazole -1'H-1'-yl) methylbenzene as a white solid (HPLC assay: 98.8 A%, 97.2 W%, overall yield: 92.4%, 0.5 W% of the regioisomer).

EXAMPLE 7

2-n-Butyl-4-chloro-1-[(2'-(2-triphenylmethyl -2H-tetrazol-5-yl)-1,1'-biphenyl-4-yl)methyl]-1H-imidazol e-5-methanol Step A: Catalyst Preparation Triphenylphosphine (262 mg, 1.0 mmol) is dissolved in THF (20 mL) and the solution is degassed by vacuum/nitrogen purges (3×). Palladium acetate (56 mg, 0.25 mmol) is added and the solution is degassed again (3×). The resulting solution is warmed to 60° C. for 30 min. and then cooled to 25° C.

Step B: Coupling

Note: All solvent must be degassed.

2-(2'-triphenylmethyl-2'H-tetrazol -5'-yl)phenylboronic acid (15.4 g, 26.7 mmol, 75 wt % pure) is suspended in diethoxymethane (DEM) (80 mL, KF ≦500 mg/ml). Water (0.55 mL, 31 mmol) is added and the slurry is aged at ambient temperature for 30 min. After the age, another charge of water (0.55 ml, 31 mmol) is added to the boronic acid suspension under agitation. The slurry is then treated with powdered potassium carbonate (8.6 g, 62 mmol) and alkylated imidazole, the titled product of Example 6 (8.97 g, 25 mmol). The mixture is aged at 20°–25° C. for 30 min then degassed well (3×). (Note: in the pilot plant, degassing takes much longer and can be started immediately after the imidazole and carbonate are added). The catalyst solution is then charged and the mixture is heated to reflux (76°–79° C.). The reaction is complete in 2–6 hours. When the imidazole has been consumed, water (30 mL) and THF (25 ml) are added and the mixture is stirred at 55°–60° C. The water layer is separated and the organic layer is washed with water (30 mL). The organic layer is concentrated in vacuo to a volume of 50 ml to remove most of the THF. More DEM (50 ml) is added and removed by distillation to further reduce THF to <5 vol%. The residual organic solution is diluted with warm (60° C.) DEM (to a final volume of 75 ml) and water (0.5 ml, 28 mmol). The mixture is then cooled slowly to −12° C. over 2 hours. After aging at −12° C. for 1 hour, the product is collected by filtration. The cake is washed with cold DEM (25 mL). Vacuum drying at 40° C. gave 15.5 g (93%) of the titled product (non-solvated). [Pd=600 to 1000 ppm.]

EXAMPLE 8

2-n-Butyl-4-chloro-1-[(2'-2-triphenylmethyl-2H-tetrazol-5-yl)-I 1'-biphenyl-4-yl )methyl]-1H-imidazole-5-methanol Step A: Catalyst preparation Triphenylphosphine (262 mg, 1.0 mmol) is dissolved in THF (20 mL) and the solution is degassed by vacuum/nitrogen purges (3×). Palladium acetate (56 mg, 0.25 mmol) is added and the solution is degassed again (3×). The resulting solution is warmed to 60° C. for 30 min. and then cooled to 25° C.

Step B: Coupling

Note: All solvents must be degassed.

2-2'-Triphenylmethyl-2'H-tetrazol-5'-yl)phenylboronic acid (15.4 g, 26.7 mmol, 75 wt % pure) is suspended in diethoxy- methane (DEM) (80 mL, KF ≦500 mg/ml). Water (0.55 mL, 31 mmol) is added and the slurry is aged at ambient temperature for 30 min. After the age, another charge of water (0.55 ml, 31 mmol) is added to the boronic acid suspension under agitation. The slurry is then treated with powdered potassium carbonate (8.6 g, 62 mmol) and the titled product of Example 22, the alkylated imidazole (8.97 g, 25 mmol). The mixture is aged at 20°–25° C. for 30 min then degassed well (3×). (Note: in the pilot plant, degassing takes much longer and can be started immediately after the imidazole and carbonate are added). The catalyst solution is then charged and the mixture is heated to reflux (76°–79° C.). The reaction is complete in 2–6 hours. When the imidazole has been consumed, water (30 mL) and THF (25 ml) are added and the mixture is stirred at 55°–60° C. The water layer is separated and the organic layer is washed with water (30 mL). Tributylphosphine (0.62 ml, 10 mol %) is added and the organic layer is concentrated in vacuo to a volume of 50 ml to remove most of the THF. More DEM (50 ml) is added and removed by distillation to further reduce THF to ≦5 vol %. The residual organic solution is diluted with warm (60° C.) DEM (to a final volume of 75 ml) and water (0.5 ml, 28 mmol). The mixture is then cooled slowly to −12° C. over 2 hours. After aging at −12° C. for 1 hour, the product is collected by filtration. The cake is washed with cold DEM (25 mL). Vacuum drying at 40° C. gave 15.5 g (93%) of the titled product (non-solvated). [Pd≦10 ppm].

EXAMPLE 9

2-n-Butyl -4-chloro-1-[(2'-2-triphenylmethyl-2H-tetrazol-5-yl)-1,1'-biphenyl-4-yl(methyl]-1H-imidazole-5-methanol as the methyl isobutyl ketone solvate A suspension of the titled product of Example 7 (5 g) in methyl isobutyl ketone (MIBK) (40 ml) is degassed (3×) and tributylphosphine (0.12 g, 8 mol %) is added. The mixture is heated to 85° C. at which time a homogeneous solution was obtained. Degassed water (0.135 g, 100 mol %) is then added and the solution is cooled to −10° C. over 2 hours. The heterogeneous solution is aged at −10° C. for 2 hours, the crystallized product is collected by filtration and washed with cold MIBK (−10° C., 15 ml). The recovery was 5.40 g of the rifled product (93.9%, as the MIBK solvate).

EXAMPLE 10

2-n-butyl-4-chloro -1-[(2'-tetrazol -5-yl)-1,1'-biphenyl-4-yl)-methyl]-1H-imidazole-5-methanol potassium salt Step A: Deprotection Dissolve 2.50 g of the titled product of Example 8, the methyl isobutyl ketone solvate, by adding 10 mL of 0.75M $H_2SO_4$ in 50:50 MeCN:water. Age 2 hours 25 min, 23°–25° C. Add 15 mL of water in 2 min (can be added in 30 min to an hour in larger scales), and age 1.75 hours, 23°–25° C. Filter and wash with 5 mL of 20:80 MeCN:water. There was almost no starting material left in the trityl alcohol filter cake (≦0.05 area%).

Step B: Free Acid Formation

Dilute the above filtrate with 13 mL of MeCN. The pH of the solution is 1.50. The temperature of the solution following neutralization and crystallization was 22°–24° C. After adding 1.5 mL of 3N NaOH (pH 1.75–1.65), the reaction is seeded with 20 mg of the free acid. Age 15 min. Slowly add the next 1 mL of 3M NaOH to allow for good crystal growth (on this scale, the addition time was 5–10 min). Age 30 min. Add the remaining 3M NaOH (pH 3.60–3.50). Age 1 hour. The white slurry is filtered and washed with 5 mL of 20:80 MeCN:water then 10 mL of water. A thorough water wash of the free acid filter cake is necessary to remove all the salts. The wash can be checked for $SO_4^{-2}$. The filter cake is dried in a vacuum oven at 35° C. for 18 hours with nitrogen purge. The yield of the free acid was 1.28 g (92.5%) and there was 54 mg (4%) of the free acid in the mother liquors.

Step C: Salt Formation

To 4.0 g (9.46 mmoles) of the free acid is added 10.9 ml of 0.842N KOH solution all in one portion. The slurry is aged at room temperature for 30 minutes, during which time most of the solid dissolves. The cloudy solution is filtered and the solids collected on a sintered glass funnel. The pH of the filtrate is measured at 9.05. The aqueous solution is added slowly to a refluxing azeotropic mixture of cyclohexane/isopropanol (69° C.) whereupon the ternary azeotrope cyclohexane/isopropanol/water (64° C.) begins to distill. When the solution is dry the temperature of the overhead rises to 69° and the potassium salt crystallizes.

When the water content of the pot is ≦0.05% the distillation is halted and the white slurry is cooled to room temperature. The white crystalline solid is collected on a sintered glass funnel and washed with 10–15 ml of cyclohexane/ isopropanol 67/33 and dried in a vacuum oven. (wt 3.8 g yield 95%).

Synthetic routes for the preparation of lovastatin, pravastatin, simvastatin, enalapril and lisinopril can be found in the following U.S. Pat. Nos. 4,231,938, 4,346,227, and 4,444,784, 4,374,829 and 4,555,502, respectively. For a review of syntheses for mevastatin see T. Rosen, C. H. Heathcock *Tetrahedron* 42, 4909–4951 (1986).

Utility

The hormone angiotensin II (AII) produces numerous biological responses (e.g. vasoconstriction) through stimulation of its receptors on cell membranes. For the purpose of identifying compounds such as AII antagonists which are capable of interacting with the AII receptor, a ligand-receptor binding assay was utilized for the initial screen. The assay was carried out according to the method described by [Glossmann, et al., *J. Biol. Chem.*, 249, 825 (1974)], but with some modifications. The reaction mixture contained rat adrenal cortical microsomes (source of AII receptor) in Tris buffer and 2 nM of $^3$H-AII with or without potential AII antagonist. This mixture was incubated for 1 hour at room temperature and the reaction was subsequently terminated by rapid filtration and rinsing through glass micro-fibre filter. Receptor-bound $^3$H-AII trapped in filter was quantitated by scintillation counting. The inhibitory concentration (IC$_{50}$) of potential AII antagonist which gives 50% displacement of the total specifically bound $^3$H-AII is presented as a measure of the affinity of such compound for the AII receptor (See Tables 1 and 2).

The potential antihypertensive effects of the compounds of this invention may be demonstrated by administering the compounds to awake rats made hypertensive by ligation of the left renal artery [Cangiano, et al., *J. Pharmacol. Exp. Ther.*, 208, 310 (1979)]. This procedure increases blood pressure by increasing renin production with consequent elevation of AII levels. Compounds are administered orally at 100 mg/kg and/or intravenously via a cannula in the jugular vein at 10 mg/kg. Arterial blood pressure is continuously measured directly through a carotid artery cannula and recorded using a pressure transducer and a polygraph. Blood pressure levels after treatment are compared to pretreatment levels to determine the antihypertensive effects of the compounds (See Table 1).

TABLE 1

Antihypertensive activity of 2-n-butyl-4-chloro-1-[(2'-(tetrazol-5-yl)-1,1'-biphenyl-4-yl)-methyl]-1H-imidazole-5-methanol potassium salt (Losartan)

|  | Angiotensin II Receptor Binding-IC$_{50}$ (μ molar) | Antihypertensive Effects in Renal Hypertensives Rats |  |
|---|---|---|---|
| Losartan | 0.039 | Intravenous Activity[1] | + |
|  |  | Oral Activity[2] | + |

[1]Significant decrease in blood pressure at 10 mg/kg or less
[2]Significant decrease in blood pressure at 100 mg/kg or less Compound listed in Table 2 was tested in the same manner as described for Table 1, except that in the test for antihypertensive effects in renal hypertensive rats, the compounds were administered orally at 30 mg/kg and intravenously at 3 mg/kg.

TABLE 2

Antihypertensive activity of 2-n-butyl-4-chloro-1-[(2'-(tetrazol-5-yl)-1,1'-biphenyl-4-yl)-methyl]-1H-imidazole-5-carboxylic acid (Compound 2)

|  | Angiotensin II Receptor Binding-IC$_{50}$ (μ molar) | Antihypertensive Effects in Renal Hypertensives Rats |  |
|---|---|---|---|
| Compound 2 | 0.011 | Intravenous Activity[1] | + |
|  |  | Oral Activity[2] | + |

[1]Significant decrease in blood pressure at 3.0 mg/kg or less
[2]Significant decrease in blood pressure at 30 mg/kg or less The hypotensive effects of 2-butyl-4-chloro-1-[2'-1H-tetrazol-5-yl)biphenyl-4-yl)methyl]-5-hydroxymethylimidazole sodium salt were compared before and after furosemide administration to conscious dogs. Cumulative intravenous injections of imidazole at 0.3 to 3 mg/kg did not lower blood pressure in normotensive conscious Dogs (n=4) but they were effective in inhibiting the pressor response to AII (0.1 μg/kg iv) determined at 10 min post dose. Plasma renin activity (PRA) in these animals was 1.5±0.5 ng AI/ml/hr. Four days later, furosemide was given to three of these dogs at 10 mg/kg im at 18 and 2 hours before the experiment and increased PRA to 19.9 ±7.2 ng AI/ml/hr. Imidazole was then given cumulatively iv at the same doses and caused a significant decrease in blood pressure in a dose-dependent manner. It also inhibited the pressor response to AII at the two higher doses. A similar hypotensive enhancement by furosemide was also observed with captopril at 0.3 mg/kg iv. These results indicate that diuretics enhance the hypotensive efficacy of imidazole AII blockers. Thus a combined therapy of these two classes of drugs will be likely to increase the response rate to therapy among hypertensive patients.

Angiotensin II (AII) is a powerful arterial vasoconstrictor, and it exerts its action by interacting with specific receptors present on cell membranes. In order to identify AII antagonists and determine their efficacy in vitro, the following two ligand-receptor binding assays were established.

Receptor Binding Assay Using Rabbit Aortae Membrane Preparation:

Three frozen rabbit aortae (obtained from Pel-Freeze Biologicals) are suspended in 5 mM Tris-0.25M Sucrose, pH 7.4 buffer (50 ml) homogenized, and then centrifuged. The mixture is filtered through a cheesecloth and the supernatant is centrifuged for 30 minutes at 20,000 rpm at 4° C. The pellet thus obtained is resuspended in 30 ml of 50 mM Tris-5 mM MgCl$_2$ buffer containing 0.2% Bovine Serum Albumin and 0.2 mg/ml Bacitration and the suspension is used for 100 assay tubes. Samples tested for screening are done in duplicate. To the membrane preparation (0.25 ml) there is added $^{125}$I-Sar$^1$Ile$^8$-angiotensin II [obtained from New England Nuclear] (10 ul; 20,000 cpm) with or without the test sample and the mixture is incubated at 37° C. for 90 minutes. The mixture is then diluted with ice-cold 50 mM Tris-0.9% NaCl, pH 7.4 (4 ml) and filtered through a glass fiber filter (GF/B Whatman 2.4" diameter). The filter is soaked in scintillation cocktail (10 ml) and counted for radioactivity using Packard 2660 Tricarb liquid scintillation counter. The inhibitory concentration (IC$_{50}$) of a potential AII antagonist which gives 50% displacement of the total specifically bound $^{125}$I-Sar$^1$Ile$^8$-angiotensin II is presented as a measure of the efficacy of such compounds as AII antagonists.

Receptor Assay Using Bovine Adrenal Cortex Preparation

Bovine adrenal cortex is selected as the source of AII receptor. Weighed tissue (0.1 g is needed for 100 assay tubes) is suspended in Tris.HCl (50 mM), pH 7.7 buffer and homogenized. The homogenate is centrifuged at 20,000 rpm for 15 minutes. Supernatant is discarded and pellets resuspended in buffer [Na$_2$HPO$_4$ (10 mM)-NaCl (120 mM)-disodium EDTA (5 mM) containing phenylmethane sulfonyl fluoride (PMSF)(0.1 mM)]. (For screening of compounds, generally duplicates of tubes are used). To the membrane preparation (0.5 ml) there is added 3H-angiotensin II (50 mM) (10 ul) with or without the test sample and the mixture is incubated at 37° C. for 1 hour. The mixture is then diluted with Tris buffer (4 ml) and filtered through a glass fiber filter (GF/B Whatman 2.4" diameter). The filter is soaked in scintillation cocktail (10 ml) and counted for radioactivity using Packard 2660 Tricarb liquid scintillation counter. The inhibitory concentration (IC$_{50}$) of a potential AII antagonist which gives 50% displacement of the total specifically bound $^3$H-angiotensin II is presented as a measure of the efficacy of such compounds as AII antagonists.

Receptor Assay Using Rat Brain Membrane Preparation

Membranes from rat brain (thalamus, hypothalamus and midbrain) are prepared by homogenization in 50 mM Tris HCl(pH 7.4), and centrifuged at 50,000× g. The resulting pellets are washed twice in 100 mM NaCl, 5 mM Na$_2$.EDTA, 10 mM Na$_2$HPO$_4$ (pH 7.4) and 0.1 mM PMSF by resuspension and centrifugation. For binding assays, the pellets are resuspended in 160 volumes of binding assay buffer (100 mM NaCl, 10 mM Na$_2$HPO$_4$, 5 mM Na$_2$.EDTA, pH 7.4, 0.1 mM PMSF, 0.2 mg/ml soybean trypsin inhibitor, 0.018 mg/ml o-phenanthroline, 77 mg/ml dithiothreitol and 0.14 mg/ml bacitracin. For $^{125}$I.Ile$^8$-angiotensin II binding assays, 10 μl of solvent (for total binding), Sar$^1$,Ile$^8$-angiotensin II (1 μM) (for nonspecific binding) or test compounds (for displacement) and 10 μl of [$^{125}$I]Sar$^1$,Ile$^8$-angiotensin II (23–46 pM) are added to duplicate tubes. The receptor membrane preparation (500 μl) is added to each tube to initiate the binding reaction. The reaction mixtures are incubated at 37° C. for 90 minutes. The reaction is then terminated by filtration under reduced pressure through glass-fiber GF/B filters and washed immediately 4 times with 4 ml of 5 mM ice-cold Tris HCl(pH 7.6) containing 0.15M NaCl. The radioactivity trapped on the filters is counted using a gamma counter.

Using the methodology described above, representative compounds of this invention could be evaluated and an IC$_{50}$<50 μM determined, thereby demonstrating and confirming the utility of the compounds of the invention as effective A II antagonists.

The antihypertensive effects of the compounds described in the present invention may be evaluated using the methodology described below:

Male Charles River Sprague-Dawley rats (300–375 gm) are anesthetized with methohexital (Brevital; 50 mg/kg i.p.) and the trachea is cannulated with PE 205 tubing. A stainless steel pithing rod (1.5 mm thick, 150 mm long) is inserted into the orbit of the right eye and down the spinal column. The rats are immediately placed on a Harvard Rodent Ventilator (rate—60 strokes per minute, volumn—1.1 cc per 100 grams body weight). The right carotid artery is ligated, both left and right vagal nerves are cut, and the left carotid artery is cannulated with PE 50 tubing for drug administration, and body temperature is maintained at 37° C. by a thermostatically controlled heating pad which received input from a rectal temperature probe. Atropine (1 mg/kg i.v.) is then administered, and 15 minutes later propranolol (1 mg/kg i.v.). Thirty minutes later antagonists of formula I are administered intravenously or orally. Angiotensin 11 is then typically given at 5, 10, 15, 30, 45 and 60 minute intervals and every half-hour thereafter for as long as the test compound showed activity. The change in the mean arterial blood pressure is recorded for each angiotensin II challenge and the precent inhibition of the angiotensin II response is calculated.

The effects of 2-butyl-4-chloro-1-[2'-1H-tetrazol-5-yl) biphenyl-4-yl)methyl]-5-hydroxymethylimidazole potassium salt (Losartan) were studied in a multicenter, double-blind, randomized, placebo-controlled clinical study. Losartan was administered in a 50 mg oral dose administered once daily to patients with mild to moderate hypertension (patients with a sitting diastolic blood pressure of 95–115 mmHg of a median age of 54), but with no other active medical problem that could, of itself or its treatment, affect blood pressure. After six weeks the non-responders were titrated to a 100 mg oral dose administered once daily.

The total, HDL, LDL and VLDL cholesterol levels were measured using the procedures described below:

High Density Lipoprotein Cholesterol

The high density lipoprotein (HDL) cholesterol was measured by analyzing a 2.0 mL volume of non-hemolyzed serum or EDTA plasma(heparinized plasma is not recommended), which has been separated from the cells within 30 minutes of collection. A fasting specimen of at least 12 hours is required for accurate interpretation. In most persons, the plasma cholesterol level is affected very little by a recent meal. However, in some persons an increase of up to 100 mg/dL may be induced by a recent meal. The level of cholesterol in plasma is slightly lower than serum (approximately 3%) due to the fact that the liquid EDTA dilutes the plasma slightly and it somotically draws water out of the erythrocytes.

The method used for in this procedure utilizes the precipitating properties of phosphotungstate. Addition of the HDL precipitating reagent lowers the pH of the sample to the isoelectric point for the LDL and VLDL. LDL and VLDL molecules at pH 5.7 have overall electrical neutrality.

Phosphotungstate then selectively forms insoluble ligand complexes with LDL and VLDL. Differences in ionic strength forcefully precipitate these complexes. Centrifugation removes them, leaving the HDL fraction in the supernatant. The resulting supernatant cholesterol (HDL) is then assayed for cholesterol. Cholesterol esters in the sample are hydrolyzed by cholesterol esterase to cholesterol and free fatty acids. The cholesterol produced in the reaction plus the free cholesterol present in the sample, are oxidized by cholesterol oxidase to form cholesten-3-one and hydrogen peroxide. Peroxidase catalyzes the hydrogen peroxide oxidation and 4-aminoantipyrine (4-AAP) and phenol with subsequent coupling to 3,4-dichlorophenol.

The end product is a quinoneimine dye which is read at a primary wavelength of 520 nm. The color formation is proportional to the concentration of cholesterol present. This absorbance value is then compared to the absorbance by a known calibrator. The result is then printed out directly in mg/dL.

Cholesterol

Cholesterol esters in the sample are hydrolyzed by cholesterol esterase to cholesterol and free fatty acids. The cholesterol produced in the reaction plus the free cholesterol present in the sample, are oxidized by cholesterol oxidase to form cholesten-3-one and hydrogen peroxide. Peroxidase catalyzes the hydrogen peroxide oxidation and 4-aminoantipyrine (4-AAP) and phenol with subsequent coupling to 3,4-dichlorophenol. The end product is a quinoneimine dye which is read at a primary wavelength of 520 nm. The color formation is proportional to the concentration of cholesterol present. This absorbance value is then compared to the absorbance by a known calibrator. The result is then printed out directly in mg/dL.

LDL Cholesterol

The low density lipoprotein cholesterol is computed by subtracting from the cholesterol value determined above one-fifth of the triglycerides and the HDL cholesterol value determined above. This LDL computation is valid only if the triglyceride level is less than 400 mg/dL.

The study at twelve weeks showed a decrease in total cholesterol and low density lipoprotein (LDL) cholesterol levels as shown in Table 3 below.

TABLE 3

| LABORATORY TEST | UNIT | WEEK | TREATMENT | N | BASELINE MEAN | BASELINE S.D. | TREATMENT MEAN | TREATMENT S.D. | CHANGE MEAN | CHANGE S.D. |
|---|---|---|---|---|---|---|---|---|---|---|
| TOTAL CHOLESTEROL | MG/DL | 12 | PLACEBO | 94 | 215.1 | 40.0 | 216.7 | 37.1 | 1.5 | 22.8 |
| | | | LOS 50 | 107 | 211.1 | 36.4 | 207.3 | 37.2 | -3.9 | 21.4 |
| | | | LOS 50/100 | 106 | 212.6 | 38.8 | 204.8 | 34.9 | -7.9 | 23.6 |
| HDL CHOLESTEROL | MG/DL | 12 | PLACEBO | 94 | 51.1 | 11.3 | 51.2 | 10.8 | 0.1 | 5.9 |
| | | | LOS 50 | 107 | 52.5 | 15.3 | 52.1 | 14.3 | -0.4 | 7.9 |
| | | | LOS 50/100 | 106 | 52.9 | 16.5 | 52.3 | 15.5 | -0.5 | 6.6 |
| LDL CHOLESTEROL | MG/DL | 12 | PLACEBO | 90 | 131.3 | 36.9 | 129.2 | 34.4 | -2.0 | 21.5 |
| | | | LOS 50 | 102 | 127.7 | 31.6 | 123.5 | 32.0 | -4.2 | 18.7 |
| | | | LOS 50/100 | 95 | 126.3 | 35.5 | 117.9 | 31.9 | -8.4 | 21.4 |
| TRIGLYCERIDES | MG/DL | 12 | PLACEBO | 94 | 166.0 | 95.3 | 186.3 | 116.4 | 20.3 | 71.4 |
| | | | LOS 50 | 107 | 170.4 | 156.7 | 173.1 | 140.9 | 2.7 | 68.5 |
| | | | LOS 50/100 | 106 | 174.4 | 105.4 | 187.8 | 139.1 | 13.4 | 102.0 |
| PLASMA RENIN ACTIVITY | NG/ML/HR | 12 | PLACEBO | 81 | 1.028 | 0.918 | 1.210 | 1.688 | 0.181 | 1.752 |
| | | | LOS 50 | 99 | 1.300 | 1.114 | 2.889 | 2.884 | 1.589 | 2.341 |
| | | | LOS 50/100 | 96 | 1.473 | 2.253 | 3.724 | 5.242 | 2.251 | 3.690 |

Sitting Diastolic Blood Pressure Results At Week 6 and 12

The changes from baseline blood pressure (primary=trough sitting diastolic blood pressure at weeks 6 and 12) were evaluated using a least squares analysis of the means based upon an analysis of covariance (covariate=baseline blood pressure) for a randomized block (block=investigator site) design. An "all-patients-treated" and a "per-protocol" analysis were performed. The study was designed to detect a 5 mmHg difference in mean change between treatments with 95% probability based upon a group size of 86 with an α of 0.05 (two-sided) and a standard deviation of 9 mmHg. The data are presented below in Tables 4, 5 and 6:

TABLE 4

Mean Change in Trough (24 hours postdose) Sitting Diastolic Blood Pressure At Weeks 6 and 12 (mmHg) All-Patient-Treated Approach

| | N | Mean | s.d. | Mean | s.d. | Mean | s.d. | adj. mean |
|---|---|---|---|---|---|---|---|---|
| 6 wk Treatment | | | | | | | | |
| placebo | 114 | 101.3 | 4.9 | 97.8 | 7.5 | -3.5 | 5.8 | -3.5 |
| losartan 50 mg | 125 | 102.1 | 5.1 | 95.3 | 8.6 | -6.9 | 7.0 | -6.9 |
| losartan 50/100 mg | 118 | 102.2 | 5.0 | 94.3 | 8.4 | -7.9 | 7.1 | -7.9 |
| 12 wk Treatment | | | | | | | | |
| placebo | 114 | 101.3 | 4.9 | 97.0 | 7.7 | -4.3 | 6.7 | -4.5 |
| losartan 50 mg | 125 | 102.1 | 5.1 | 94.2 | 9.0 | -7.9 | 7.6 | -7.9 |
| losartan 50/100 mg | 118 | 102.2 | 5.0 | 93.6 | 8.3 | -8.6 | 7.7 | -8.6 |

TABLE 5

Mean Change in Peak (6 hours postdose) Sitting Diastolic Blood Pressure At Weeks 6 and 12 (mmHg) All-Patient-Treated Approach

| | N | Mean | s.d. | Mean | s.d. | Mean | s.d. | adj. mean |
|---|---|---|---|---|---|---|---|---|
| 6 wk Treatment | | | | | | | | |
| placebo | 108 | 98.6 | 6.3 | 94.5 | 7.7 | -4.1 | 6.9 | -4.2 |
| losartan 50 mg | 118 | 99.9 | 7.1 | 90.2 | 10.5 | -9.7 | 8.7 | -9.7 |
| losartan 50/100 mg | 111 | 99.1 | 5.9 | 90.3 | 9.6 | -8.9 | 8.7 | -9.0 |
| 12 wk Treatment | | | | | | | | |
| placebo | 108 | 98.6 | 6.3 | 93.9 | 8.8 | -4.7 | 7.9 | -4.6 |

TABLE 5-continued

Mean Change in Peak (6 hours postdose) Sitting Diastolic Blood Pressure At Weeks 6 and 12 (mmHg) All-Patient-Treated Approach

|  | N | Mean | s.d. | Mean | s.d. | Mean | s.d. | adj. mean |
|---|---|---|---|---|---|---|---|---|
| losartan 50 mg | 121 | 99.8 | 7.1 | 90.3 | 10.5 | −9.5 | 9.2 | −9.3 |
| losartan 50/100 mg | 113 | 99.2 | 6.0 | 89.1 | 9.1 | −10.1 | 8.6 | −10.1 |

TABLE 6

Categories of Antihypertensive Response (Trough SDBP) At Weeks 6 and 12

|  | Category I: Trough SDBP <90 mmHg | Category II: Trough SDBP ≥90 mmHg | Category III: Neither Category I or II | Total |
|---|---|---|---|---|
| 6 wk Treatment |  |  |  |  |
| placebo | 14 (12.2%) | 8 (7.0%) | 92 (80.7%) | 114 (100%) |
| losartan 50 mg | 37 (29.6%) | 20 (16.0%) | 68 (54.4%) | 125 (100%) |
| losartan 50/100 mg | 37 (31.3%) | 21 (17.7%) | 60 (50.8%) | 118 (100%) |
| 12 wk Treatment |  |  |  |  |
| placebo | 19 (16.6%) | 12 (10.5%) | 83 (72.8%) | 114 (100%) |
| losartan 50 mg | 40 (32.0%) | 18 (14.4%) | 67 (53.6%) | 125 (100%) |
| losartan 50/100 mg | 37 (31.3%) | 24 (20.3%) | 57 (48.3%) | 118 (100%) |

DOSAGE FORMS

The compounds of this invention can be administered for the treatment of hypertension according to the invention by any means that effects contact of the active ingredient compound with the site of action in the body of a warm-blooded animal. For example, administration can be parenteral, i.e., subcutaneous, intravenous, intramuscular or intra peritoneal. Alternatively, or concurrently in some cases administration can be by the oral route.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1–500 milligrams per day. Ordinarily, from 10 to 100 milligrams per day in one or more applications is effective to obtain desired results. These dosages are the effective amounts both for treatment of hypertension and for treatment of congestive heart failure, i.e., for lowering blood pressure and for correcting the hemodynamic burden on the heart to relieve the congestion.

The active ingredient can be administered orally in solid dosage forms, such as capsules, tablets, and powders, or in liquid dosage forms, such as elixirs syrups, and suspensions. It can also be administered parenterally, in sterile liquid dosage forms.

Gelatin capsules contain the active ingredient and powdered carriers, such as lactose, starch, cellulose derivatives, magnesium stearate, stearic add, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gyclols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

CAPSULES

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

SOFT GELATIN CAPSULES

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol. The solution is made to volume with water for injection and sterilized.

SUSPENSION

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Suitable dosages, dosage forms and administration routes are illustrated in Tables 7 and 8.

TABLE 7

Examples of HMG-Co A reductase inhibitors of formula II that can be combined with AII blockers of formula I for the treatment of atherosclerosis

| Drug | Dose (mg) | Formulation | Route of Admin. |
|---|---|---|---|
| lovastatin | 10, 20, 40 mg/day | Tablet | Oral |
| simvastatin | 5, 10, 20, 40 mg/day | Tablet | Oral |

TABLE 8

Examples of ACE inhibitors that can be combined with an A II blocker of formula I and an HMG-Co A reductase inhibitor of formula II useful for the treatment of atherosclerosis

| Drug | Dose (mg) | Formulation | Route of Admin. |
|---|---|---|---|
| lisinopril | 5, 10, 20, 40 mg/day | Tablet | Oral |
| enalapril | 10–40 mg/day | Tablet | Oral |

What is claimed is:

1. A method of treating atherosclerosis and reducing cholesterol alone or in conjunction with the treatment of hypertension using an angiotensin II antagonist of formula I, wherein the angiotensin II antagonist of formula I is selected from the group consisting of:

2-butyl-4-chloro-1-[(2'-tetrazol-5-yl)biphenyl-4-yl] methyl]-5-hydroxymethyl)imidazole; and 2-butyl-4-chloro -1-[(2'-tetrazol-5-yl)biphenyl-4-yl] methylimidazole-5-carboxylic acid; and an HMG-CoA reductase inhibitor of formula II, wherein the HMG-CoA reductase inhibitor of formula II is selected from the group consisting of: lovastatin, simvastatin and pravastatin, or their pharmaceutically acceptable salts.

2. A pharmaceutical composition useful for the treatment of atherosclerosis and reducing cholesterol alone or in conjunction with the treatment of hypertension which comprises a pharmaceutically acceptable carrier and a pharmaceutically effective mount of an angiotensin II antagonist of formula I, wherein the angiotensin II antagonist of formula I is selected from the group consisting of: 2-butyl-4-chloro-1-[(2'-tetrazol-5-yl)biphenyl-4-yl]methyl]-5-hydroxymethyl)imidazole; and 2-butyl-4-chloro-1-[(2'-tetrazol-5-yl) biphenyl-4-yl]methylimidazole-5-carboxylic acid; and an HMG-CoA reductase inhibitor of formula II, wherein the HMG-CoA reductase inhibitor of formula II is selected from the group consisting of: lovastatin, simvastatin and pravastatin, or their pharmaceutically acceptable salts.

* * * * *